United States Patent [19]

Osterholm

[11] 4,446,154
[45] May 1, 1984

[54] STROKE TREATMENT UTILIZING EXTRAVASCULAR CIRCULATION OF OXYGENATED SYNTHETIC NUTRIENTS TO TREAT TISSUE HYPOXIC AND ISCHEMIC DISORDERS

[75] Inventor: Jewell L. Osterholm, Radnor Township, Delaware County, Pa.

[73] Assignee: Thomas Jefferson University, Philadelphia, Pa.

[21] Appl. No.: 428,685

[22] Filed: Sep. 30, 1982

Related U.S. Application Data

[60] Division of Ser. No. 354,346, Mar. 3, 1982, which is a continuation-in-part of Ser. No. 275,117, Jun. 18, 1981, Ser. No. 275,116, Jun. 18, 1981, Pat. No. 4,393,863, and Ser. No. 139,886, Apr. 14, 1980, Pat. No. 4,378,797, said Ser. No. 275,117, and Ser. No. 275,116, each is a division of Ser. No. 139,886.

[51] Int. Cl.³ .................... A61K 31/00; A61M 5/14
[52] U.S. Cl. ................................ 424/350; 424/355
[58] Field of Search ............... 424/153, 355; 425/350, 425/325

[56] References Cited

U.S. PATENT DOCUMENTS

| | | | |
|---|---|---|---|
| 3,482,575 | 12/1969 | Claff et al. | 128/214 |
| 3,516,410 | 6/1970 | Hakim | 128/350 |
| 3,583,387 | 6/1971 | Garner | 128/1 |
| 3,626,950 | 12/1971 | Schulte | 128/350 |
| 3,669,094 | 6/1972 | Heyer | 128/2 |
| 3,669,116 | 6/1972 | Heyer | 128/350 |
| 3,690,323 | 9/1972 | Wortman et al. | 128/350 |
| 3,753,865 | 8/1973 | Belzer | 195/127 |
| 3,823,091 | 7/1974 | Samejima | 252/312 |
| 3,894,541 | 7/1975 | El-Shafei | 128/350 |
| 3,941,119 | 3/1976 | Corrales | 128/2 |
| 3,946,731 | 3/1976 | Lichtenstein | 128/214 |
| 3,989,843 | 11/1976 | Chabert et al. | 424/325 |
| 4,110,474 | 8/1978 | Lagow et al. | 424/350 |
| 4,148,314 | 4/1979 | Yin | 128/214 |
| 4,163,734 | 4/1979 | Sorensen et al. | 252/408 |
| 4,173,224 | 11/1979 | Marx et al. | 128/214 |
| 4,173,654 | 11/1979 | Scherer | 424/350 |

OTHER PUBLICATIONS

S. A. Gould et al., *Fed. Proc.*, 40:2038, (1981).
Doss et al., *Microvascular Research* 13, pp. 253–260, (1977).
Nordstrom et al., *Acta Physiol. Scand.*, (1977).
Siezyo et al., *Adv. Exp. Med. Biol.*, 78; 261–269, (1977).
Clark et al., *Microvasc. Res.*, 8:320–340, (1974).
Abstract No. [85] Pool Rounds (one page).
Booklet "William Harvey Introduces a New Geometry for Oxygen Performance."
State of the Art Symposium "Artificial Blood", National Institutes of Health, Apr. 5–6, 1974, Federation Proceedings, vol. 34, No. 6, pp. 1428–1517, (1975).
Tsuyumu et al., "Dynamics of Formation and Resolution of Vasogenic Brain Oedema I. Measurement of Oedema Clearance into Ventricular CSF", *Acta Neurochirurgica*, 57:1–13, (1981).
Tremper et al., "The Preoperative Treatment of Severely Anemic Patients with a Perfluorochemical Blood Substitute, Fluosol-DA 20%", *Crit. Care Med.*, 8, p. 738, (1980).
Weyne et al., "Restoration of CSF[HCO₃] After its Experimental Lowering in Normocapnic Conditions", *J. of Applied Physics*, vol. 47, pp. 369–376, (Jul.–Sep. 1979).
Schutz et al., "Brain Mitochondrial Function After Ischemia and Hypoxia", *Arch Neurol.*, vol. 29, pp. 417–419, (Dec. 1973).
Sokoll et al., "Dibutyryl Cyclic Adenosine Monophosphate Effects in the Ischemic-Hypoxic Cat", *Stroke*, vol. 8, No. 3, pp. 371–373, (May–Jun. 1977).
J. Suzuki et al., *Current Topics*, 9:465–479, (1981).
Mizoi et al., "Experimental Study of New Cerebral Protective Substances-Functional Recovery of Severe, Incomplete Ischaemic Brain Lesions Pretreated with Mannitol and Fluorocarbon Emulsion", *Acta Neurochirurgica* 56, pp. 157–166, (1981).
Peerless et al., "Protective Effect of Fluosol-DA in Acute Cerebral Ischemia", *Stroke*, vol. 12, No. 5, pp. 558–563, (1981).
Reulen et al., "Clearance of Edema Fluid into Cerebrospinal Fluid", *J. Neurosurg,* , 48: 754–764, (1978).
Kleihues et al., "Purine Nucletide Metabolism in the Cat Brain After One Hour of Complete Ischemia", *Journal of Neurochemistry*, vol. 23, pp. 417–425, (1974).

Min-Chu Liew et al., "A Technique for Perfusing the Cerebrospinal Fluid Spaces of the Cat from Lateral Ventricle via the Cisterna Magna to the Cortical Subarachnoid Space", *J. Physiol.*, pp. 20P–21P, (1977).
Martins et al., "Sources of Error in Measuring Cerebrospinal Fluid Formation by Ventriculocisternal Perfusion", *Journal of Neurosurgery and Psychiatry*, vol. 40, pp. 645–650, (1977).
Hossman et al., "Resuscitation in the Monkey Brain After 1 H Complete Ischemia. 1. Physiological and Morphological Observations", *Brain Research*, 81:59–74, (1974).
Hossmann et al., "Reversibility of Ischemic Brain Damage", *Arch. Neurol.*, vol. 29, pp. 375–384, (Dec. 1973).
Javid et al., "Hypothermic Ventricular Perfusion—Evaluation of Use in Cerebrovascular Occlusion", *New York State Journal of Medicine*, pp. 248–251, (Jan. 15, 1967).
Kleihues, et al., "Purine Nucletide Metabolism in the Cat Brain After One Hour of Complete Ischemia", *Journal of Neurochemistry*, vol. 23, pp. 417–425, (1974).
Min-Chu Liew et al., "A Technique for Perfusing the Cerebrospinal Fluid Spaces of the Cat from Lateral Ventricle via the Cisterna Magna to the Cortical Subarachnoid Space", *J. Physiol*, pp. 20P–21P, (Dec. 1977).
Martins, et al., "Sources of Error in Measuring Cerebrospinal Fluid Formation by Ventriculocisternal Perfusion", *Journal of Neurosurgery and Psychiatry*, vol. 40, pp. 645–650, (1977).
Mizoi et al., "Experimental Study of New Cerebral Protective Substances Functional Recovery of Severe, Incomplete Ischaemic Brain Lesions Pretreated with Mannitol and Fluorocarbon Emulsion *Acta Neurochirurgica* 56, pp. 157–166, (1981).
Peerless et al., "Protective Effect of Fluosol-DA in Acute Cerebral Ischemia", *Stroke*, vol. 12, No. 5, pp. 558–563, (1981).
Reulen, et al., "Clearance of Edema Fluid into Cerebrospinal Fluid", *J. Neurosurg* 48: 754–764, (1978).
Schutz, et al., "Brain Mitochondrial Function After Ischemia and Hypoxia", *Arch Neurol*, vol. 29, pp. 417–419, (Dec. 1973).
Sokoll et al., "Dibutyryl Cyclic Adenosine Monophosphate Effects in the Ischemic-Hypoxic Cat", *Stroke*, vol. 8, No. 3, pp. 371–373, (May–Jun. 1977).
J. Suzuki et al., *Current Topics* 9:465–479, (1981).
Tsuyumu, et al., "Dynamics of Formation and Resolution of Vasogenic Brain Oedema I. Measurement of Oedema Clearance into Ventricular CSF", *Acta Neurochirurgica* 57:1–13, (1981).
Tremper et al., "The Preoperative Treatment of Severely Anemic Patients with a Perfluorochemical Blood Substitute, Fluosol-DA 20%", *Crit. Care Med.* 8, p. 738, (1980).
Weyne et al., "Restoration of CSF[HCO$_3$] After its Experimental Lowering in Normocapnic Conditions", J. of Applied Physics, vol. 47, pp. 369–376, (Jul.–Sep. 1979).
Abstract No. [85] Pool Rounds, (one p.).
Booklet, "William Harvey Introduces a New Geometry for Oxygen Performance."
State of the Art Symposium, "Artificial Blood", National Institutes of Health, Apr. 5–6, 1974, Federation Proceedings, vol. 34, No. 6, pp. 1428–1517, (1975).
Nordstrom et al., *Acta Physiol. Scand.*, (1977).
Siezyo et al., *Adv. Exp. Med. Biol.* 78; 261–269, (1977).
Clark et al., *Microvasc. Res.* 8:320–340, (1974).
S. A. Gould et al., *Fed. Proc.* 40:2038, (1981).
Doss et al., Microvascular Research 13, pp. 253–260, (1977).

*Primary Examiner*—George F. Lesmes
*Assistant Examiner*—Nancy A. B. Swisher
*Attorney, Agent, or Firm*—Woodcock, Washburn, Kurtz, Mackiewicz & Norris

[57] ABSTRACT

A novel acute care cerebral support system and method for treating severly ischemic brains is disclosed wherein an oxygenated nutrient emulsion is circulated through at least a portion of the ventriculo-subarachnoid spaces. The nutrient emulsion contains an oxygenatable non-aqueous component, an aqueous nutrient component, an emulsification component, and other components which render physiologic acceptability to the nutrient emulsion. The disclosed system and method have been shown to effectively exchange oxygen, carbon dioxide, glucose, and other metabolites in severely stroked brains. Significant restoration of oxidative metabolism and electrographic activity result from the disclosed treatment. Methods for producing the nutrient emulsion and a system for delivering that emulsion to the cerebrospinal pathway are also disclosed. Additionally, novel diagnostic methods for diagnosing the physiologic state of hypoxic-ischemic and other diseased neurologic tissue during treatment are provided.

20 Claims, 13 Drawing Figures

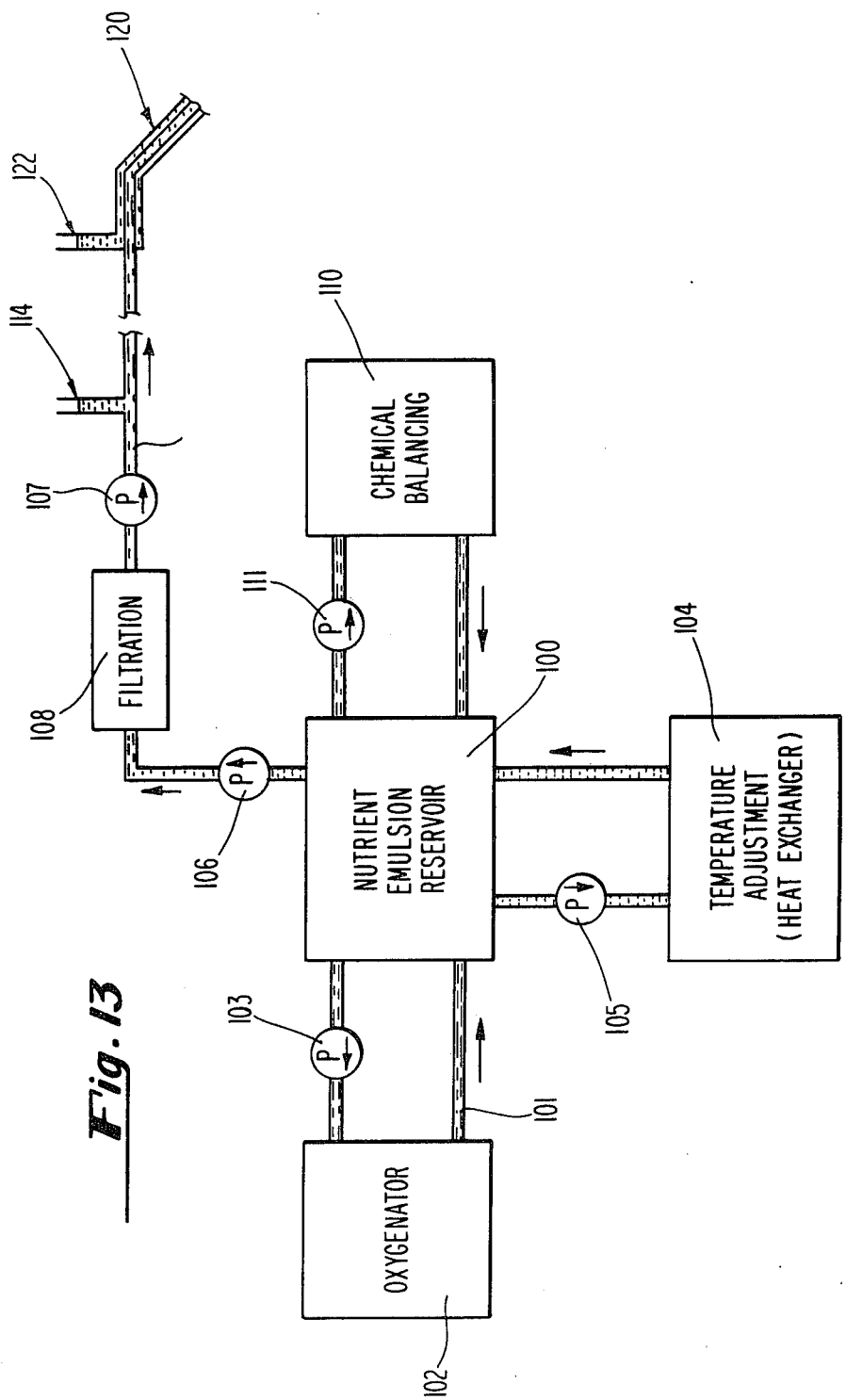

STROKE TREATMENT UTILIZING EXTRAVASCULAR CIRCULATION OF OXYGENATED SYNTHETIC NUTRIENTS TO TREAT TISSUE HYPOXIC AND ISCHEMIC DISORDERS

CROSS REFERENCE TO RELATED APPLICATIONS

The present application is a divisional application of Ser. No. 354,346, filed Mar. 3, 1982, which is a continuation-in-part of U.S. patent application Ser. No. 139,886, filed Apr. 14, 1980, now U.S. Pat. No. 4,378,797, entitled "Extravascular Circulation Oxygenated Synthetic Nutrients to Treat Tissue Hypoxic and Ischemic Disorders", as well as Ser. No. 275,116, filed June 18, 1981, now U.S. Pat. No. 4,393,863 and Ser. No. 275,117, also filed June 18, 1981, which in turn are divisionals of Ser. No. 139,886. These applications are hereby incorporated by reference as if fully set forth herein.

BACKGROUND OF THE INVENTION

Cerebrovascular accident, a disease commonly known as "stroke", remains the third leading cause of death, and probably constitutes the single largest category of long term disability in this country. In spite of current medical knowledge and available treatments, a major central nervous system vascular occlusion is quickly attended by irreversible damage to the affected brain region(s). A "completed stroke" is manifest by a fixed and permanent neurological deficit. Millions of dollars have been expended in stroke research and care by Federal and private agencies without a single substantial gain in our present chemotherapeutic abilities for a completed stroke.

On a clinical level, once vascular flow in any portion of the central nervous system has ceased for longer than a few minutes, a permanent "stroke" invariably follows. It is not currently possible to recover substantial neural function with clinical ischemia of 5-7 minutes duration. An exquisite neuronal sensitivity to oxygen deprivation has been blamed for this ultra-short stroke irreversibility. Neurons do indeed have meager metabolic storage and are unable to meet energy needs by anerobic means. Well accepted concepts hold that such permissible cerebral ischemia times are critical and neurons must quickly be resupplied or metabolic infarction will result. While clinically true, recent laboratory investigations have addressed the problems of ischemic vascular and neuronal reactions separately with considerably different results. Recently reported studies indicate neurons are not as sensitive as previously believed. Indeed, it has been suggested that neurons can withstand global ischemia for 1 hour or longer. K. A. Hossman, P. Kleihues, *Arch. Neurol.* 29, 375-389 (1973). If the clinical and experimental observations are to be reconciled, one hypothesis is that long-term damage results from vascular rather than neuronal sensitivity to oxygen deprivation. It is known that secondary reactive changes appear within the microcirculation after sufficient stagnation. A. Ames III, R. L. Wright, M. Kowada, J. M. Thurston, G. Majno, *Am. J. Pathol.* 52, 437-448, (1968). J. Chiang, M. Kowada, A. Ames III, *Am. J. Pathol.* 52, 455-476 (1968). E. G. Fischer, *Arch Neurol.* 29, 361-366, (1973). E. G. Fischer, A. Ames III, E. T. Hedly-Whyte, S. O'Gorman, *Stroke* 8, 36-39, (1977). Even if blood is represented to the local tree, the small vessels do not completely reopen. Under these circumstances ischemic, though potentially recoverable, neurons may be lethalized because they are not adequately resupplied with blood within their metabolically tolerable limits. This concept shifts the basic fault in stroke from "ultrasensitive" neurons to a protracted blood flood failure. Nonetheless, a long felt need exists to prevent permanent damage and/or reverse neurologic deficits resulting from interrupted vascular flow.

One experimental approach which has been used to investigate the effects of stroke on neurologic tissue is the perfusion of fluids of known composition through ventriculocisternal spaces. For example, E. Fritschka, J. L. Ferguson and J.J. Spitzer have reported increases in free fatty acid turnover in cerebral spinal fluid during hypotension in dogs. According to the Fritschka technique, a "mock" cerebral spinal fluid containing radio-labelled palmitate was perfused from the lateral ventricle to the cisterna magna of conscious dogs. Arteriovenous glucose and fatty acid concentrations, and "mock" CSF fatty acid concentrations were monitored over a period of 6 hours of perfusion. Estimates of the amount of palmitate recovered from the cisternal effluent and cerebral venous blood lead to the conclusion that a sizeable fraction of free fatty acids may be taken up by tissues "in the vicinity of the CSF space". See Fritschka et al, "Increased Free Fatty Acid Turnover in CSF During Hypotension in Dogs", *American Journal of Physiology*, 232:H802-H807. In "Bulk Flow and Diffusion in the Cerebral Spinal Fluid System of the Goat", by Heise, Held, and Pappenheimer, a ventriculo cisternal perfusion method was used on chronically prepared, unanaesthized goats. Measurements were made of steady-state rates at which inulin, fructose, creatinine, urea, potassium, sodium, and labelled water were removed from perfusion fluid at various hydrostatic and osmotic pressures. The subject perfusions were carried out on female goats provided with implanted ventricular and cisternal guide tubes or cannulas. Each clearance period involved perfusion of 70-120 mills of fluid through the ventricular cisternal system. Inflow rate was maintained constant in the range of 1.50-2.00 ml-min, and outflow was measured continuously. The data obtained was used to investigate the effects of hydrostatic pressure on inulin clearance, rate of formation of CSF, and the permeability of the ventricular system, particularly as compared with that of the toad bladder. This ventriculo cisternal perfusion method was first reported by Pappenheimer, Heise, Jordan and Downer in "Perfusion of the Cerebral Ventricular in Unanaestheized Goats", *American Journal of Physiology*, Vol. 203, pp. 763-774 (1962). Pappenheimer et al reported that goats are anatomically and tempermentally suited for ventricular cisternal perfusions and can tolerate such perfusions for many hours without showing signs of discomfort. The volume of the ventricular system and rate of production of CSF are at least double corresponding values reported for large dogs, and the thickness of the goat occipital bone and its shape facilitates retrograde placement of cannulas through the occipital bone into or above the cisterna magna without interfering with muscles in the neck. The goat's horns provide natural mechanical protection for the cannulas and "are almost indispensable" for operative procedures. In accordance with the Pappenheimer et al technique, guide tubes are implanted just above the dura over the cisterna magna and just above the ependymal linings of the lateral ventricules. Prior to each perfusion the cisterna and ventricle are punctured with sharp probe needles extending a few millimeters beyond the tips of the guide tubes. Alternatively, cannulas were implanted in the subarachnoid space over the parietal cortex, thus permitting perfusion of the entire ventriculo cisternal-subarachnoid system. Pappenheimer et al followed detailed protocols for implanting the guide tubes, and for preparing sterile, synethetic CSF. The Pappenheimer et al perfusion circuit is reported to comprise a bottle sealed with a rubber cap having two stainless steel tubes extending to the bottom of the bottle. One tube serves as a gas bubbler, the second as a liquid outlet. A third opening connects with atmosphere through a sterile cotton plug. The bottle is mounted on an indicating balance and the reservoir outflow is connected through tubing to a parastalic pump with a variable drive permitting pumping rates in the range of 0.5–5 ml/min. One pump output is lead to a male syringe joint which fits the ventricular probe needles and a second outlet on the joints connects to a strain gauge manometer. A 5 ml empty sterile syringe is placed in parallel with the output to damp pulsations of the pump. The cisternal outflow is connected to an enclosed drop counter and wing flask and the output is recorded cumulatively on a polygraph which also gives a vertical record proportional to outflow rate. Pappenheimer et al reports that perfusion with CSF of normal composition can usually be maintained for 4–8 hours before the animal becomes resistive, and if correctly performed, the animal will show no sign of knowing when the perfusion pump is on or off. No attempt is made to regulate the temperature of fluid entering the ventricular probe, however at flow rates of 1–2 ml/min it is theorized that the fluid reaches temperature equilibrium with the brain before reaching the hypothalmus. At higher flow rates (4–6 ml/min) the animals are reported to start to shiver. In this regard, see also F. H. Sklar and D. M. Long, *Neurosurgery* 1, 48–56 (1977).

Over the years, many experiments have been conducted with materials possessing high oxygen-dissolving properties, many of which have been incorporated as constituents in "artificial blood". The concept of utilizing materials possessing high oxygen-dissolving properties for the maintenance of tissue respiration was first reported by Rodnight in 1954. See Rodnight, R., *Biochemistry Journal*, Vol. 57, p. 661. Rodnight capitalized upon the considerable oxygen solubility found in silicone oils, and sustained tissue slices by incubation in these oxygen laden oils. Approximately 12 years later, Clark reported experiments involving the total immersion of small animals in silicone oils and fluorocarbon liquids. Rats totally immersed in oxygenated silicone oil survived for one hour with no apparent ill effects, but died several hours after removal, from unknown causes. Similar experiments using synthetic fluorocarbon liquids, which dissolve about 3 times more oxygen than do the silicone oils, were performed with some success. Under these conditions animals survived immersion in oxygenated synthetic fluorocarbon liquids and thereafter returned to apparent health. See Clark, L. C. Jr. and Gollon F., *Science*, Vol. 152, p. 1755, (1966); and Gollon, F., Clark, L. C. Jr., *Alabama Journal of Medical Science*, Vol. 4, p. 336, (1967). While arterial oxygenation was reported as excellent for Clark's studies in rats, coincident impairment of carbon dioxide elimination was also reported, as was pulmonary damage from breathing fluorocarbon liquids. One rat, which was observed for five days following liquid breathing, was described as being in respiratory distress and as succumbing within 15 minutes after the subcutaneous administration of hydrocortisone (50 mg), with copious loss of body fluid from the trachea. In this regard, Clark concluded:

These organic liquids should prove to be of value in studies of gas exchange in living tissues in animals. Organic liquids, since they can support respiration with oxygen at atmospheric pressure and have other unique qualities, may find use in submarine escape, undersea oxygen support facilities, and medical application. The pulmonary damage caused by the breathing of the organic liquids available at the present time remains a major complication of their use in man. *Science*, Vol. 152., p. 1756.

See also K. K. Tremper, R. Lapin and E. Levine, *Critical Care Medicine* 8:738 (1980); S. A. Gould, A. L. Rosen, L. R. Sehgal, *Fed. Proc.* 40:2038 (1981).

Following these observations, fluorocarbon liquids were used as an incubation medium for isolated rat hearts. See Gollon and Clark, *The Physiologist*, Vol. 9, p. 191, (1966). In this work, myocardial oxygen requirements were apparently well met, however these hearts did not flourish without intermittent fluorocarbon removal and washing with oxygenated, diluted blood. This phenomenon has been explained in terms of aqueous phase lack in pure fluorocarbons such that necessary ionic exchange is impeded.

More recently, considerable attention has been directed to the use of fluorocarbons as constituents of artificial blood. Sloviter, in order to overcome the problem of aqueous-metabolite fluorocarbon insolubility, made an emulsion with fluorocarbon and albumin. Sloviter's emulsion sustained the isolated rat brain by a vascular perfusion as well as did an erythrocyte suspension. See Sloviter, H. A. and Kamimoto T., *Nature* (London), Vol. 216, p. 458 (1967). A better emulsion was later developed comprising a detergent, "Pluronic F 68" (manufactured by the Wyandotte Chemical Corp., Wyandotte, Mich.), and fluorocarbon liquids which were properly emulsified using sonic energy. This improved emulsion permitted the replacement of most of the blood of a rat which was then reported as surviving in an atmosphere of oxygen for five to six hours. See Geyer "Survival of Rats Totally Perfused with a Fluorocarbon-Detergent Preparation", *Organ Perfusion and Preservation*, edited by V. C. Normen, N.Y.: Appelton-Century-Crofts, pp. 85–96 (1968), Geyer, R. P., *Federation Proceedings*, Vol. 29, No. 5, September–October, 1970; and Geyer, R. P. *Med u Ernohn*, Vol. 11, p. 256 (1970).

Experiments have also been reported wherein fluorocarbons have been used to perfuse livers. Ten hours after in vitro fluorocarbon perfusion, the isolated liver ATP; AMP; lactate/pyruvate ratio; and a number of other metabolites were found to be as good or better than livers perfused in vitro with whole blood. See Krone W., Huttner, W. B., Kampf S. C. et al., *Biochemika et Biophysica Acta*, Vol. 372, pp. 55–71 (1974). These detailed metabolic studies indicated that the organs perfused with 100% fluorocarbon liquid were redeemed "intact"; while only 75% of the whole blood infused organs maintained a similar degree of metabolic integrity. The ability of fluorocarbon perfusion to maintain cellular integrity was confirmed by electron-microscopy studies. The cells had normal mitochondrial ultra structure after ten hours of fluorocarbon support, indicating the persistence of normal or adequate aerobic metabolism. In Brown and Hardison, "Fluorocarbon Sonicated as a Substitute for Erythocytes in Rat Liver Perfusion", *Surgery* 71, pp. 388-394 (1972) a fluorocarbon perfusate preserved organ function and integrity far better than perfusate with much lower oxygen carrying capacity, but was reported as resulting in a decreased rate of bile secretion which was probably the earliest sign of hepatic damage, tissue edema, and a reproducible rise of portal pressure over a period of 2½ to 3 hours. Both tissue edema and rising portal pressure with fluorocarbon perfusion were associated with progressive vascular occlusion as determined histogolically. A greatly diminished perfusion of fluorocarbon at the end of experiments was documented by injection of India ink twenty minutes before the end of the perfusion. Brown and Hardison hypothesized that the fluorocarbon perfusate may react with amino acids and proteins, that the oxygen concentration in the fluorocarbon perfusate may affect the perfusion results, and that filtration of the fluorocarbon emulsion through filter paper and differing instrumentation were responsible for the apparently conflicting results in the literature. Brown and Hardison hypothesize that phagocytosis of fluorocarbon particles might completely block reticticuloendotheilial cells in liver or that capillary endotheilial damage may be another reason for late fluorocarbon perfusion problems.

Fluorocarbons have also been used in experiments involving cerebral blood circulation. In Rosenblum's studies, mouse hematocrits were reduced to 10-15 by exchanging the animal's blood with a fluorocarbon solution. When the animals were respired with 100% oxygen after intravascular fluorocarbon infusions, the brains remained metabolically sound. These organs were able to reverse rising NADH levels and EEG abnormalities induced by short period nitrogen inhalation. The EEG's of fluorocarbon treated animals could be activated by the central nervous system stimulant metrazole. By these criteria, intravascular fluorocarbon does support the cerebral microcirculation and provides functions of oxygenation, metabolism and electrical activity which are normally associated with blood transport. Please refer to Rosenblum, W. I., "Fluorocarbon Emulsions and Cerebral Microcirculation", *Federation Proceedings*, Vol. 34, No. 6, p. 1493 (May 1975). See also S. J. Peerless, R. Ishikawa, I. G. Hunter, and M. J. Peerless, *Stroke* 12, pp. 558-563 (1981); B. Dirk, J. Creiglstein, H. H. Lind, H. Reiger, H. Schultz, *J. of Pharm. Method* 4, pp. 95-108 (1980); J. Suzuki, T. Y. Oshomoto, S. Tanaka, K. Moizoi, S. Kagawa, *Current Topics* 9, pp. 465-470 (1981).

As reported by Kontos et al, the marked vasodilation of small cerebral surface arteries which occurs in response to acute profound hypoxemia may be locally obviated by perfusing oxygen equilibrated fluorocarbon into the space under the cranial window. See Kontos, H. A., et al, "Role of Tissue Hypoxemia in Local Regulation of Cerebral Microcirculation", *American Journal of Physiology*, Vol. 363, pp. 582-591 (1978). Kontos et al described the effect of perfusions with fluorocarbon with 100% oxygen as resulting from increased supplies of oxygen to the neural cells and consequent partial or complete relief of hypoxia, rather than to a local increase in the oxygen tension in the immediate environment of the vascular smooth muscle of the pial arterioles. Two other potential explanations for the observed action are also suggested in the Kontos et al article.

In 1977, Doss, Kaufman and Bicher reported an experiment wherein a fluorocarbon emulsion was used to partially replace cerebrospinal fluid, with the intention of evaluating its protective effect against acute anoxia. Doss et al, *Microvascular Research* 13, pp. 253-260 (1977). According to this experiment, systemic hypoxia was produced through one minute of 100% nitrogen inhalation. A bolus of oxygenated fluorocarbon placed in the cisterna magna immediately prior to nitrogen breathing increased regional cerebrospinal fluid $O_2$ tension by a factor of 5. During the one minute experimental period, the fluorocarbon emulsion provided twice as much brain tissue oxygen as was found in saline injected controls. Doss et al found the anticipated regional tissue oxygenation decline attending nitrogen inhalation to be halved by the administration of the oxygen bearing fluorocarbon emulsion.

In spite of the above described experiments, there is yet to be reported any practical therapeutic approach to the treatment of ischemic neurologic tissue, and particularly human ischemic central nervous system tissue resulting from stroke, accident or disease.

SUMMARY OF THE INVENTION

The present invention provides a novel nutrient formulation for circulation through cerebrospinal fluid pathways, and systems and methods for using same, to treat central nervous tissue hypoxic-ischemic conditions. Through its use, a new diagnostic methodology is also disclosed.

Applicant has recognized that there is a therapeutic time window through which neuron can be reached and resuscitated. The method of the present invention is designed to bypass obstructed vascular circulation and deliver cerebral metabolic needs through an alternate cerebral spinal fluid (CSF) circulation portal. Since particle size exerts a major influence on brain penetration from CSF, the method of the present invention is hypothesized to permit diffusion of oxygen, glucose, electrolytes and essential amino acids into ischemic neural tissue when presented in abundance in the cerebral spinal pathway. Thus, a rapidly exchanging cerebral spinal fluid perfusion system is provided to amply supply these materials and, at the same time, remove metabolic waste.

The cerebrospinal fluid (CSF) pathway system, which intimately bathes and permeates brain and spinal cord tissues, constitutes a unique anatomical relationship within the body. Although it has some similarities to systemic lymphatics, its anatomical arrangement differs considerably from that of lymph. Indeed, this system has been named the "third circulation". Due to the extensive area of CSF-tissue contact over the cerebral and cord surfaces, in the miniature Virchow-Robins spaces, and cerebral ventricles, the cerebrospinal fluid system constitutes a vast, complex and intimate therapeutic avenue for access to central nervous tissue. Excepting certain infections and neoplasms where the cerebrospinal fluid is now utilized as a treatment conduit, the cerebrospinal fluid system has not been otherwise widely exploited as an easily accessible therapeutic route and has never been used as a continuous therapeutic diagnostic circulation system in man. The present invention is predicated on the recognition that, when regional cerebral blood flow is interrupted, such as after major stroke, or is otherwise seriously impeded by profound vaso-spastic states, the cerebrospinal fluid pathway actually represents the only practical and viable anatomical route by which these tissues may be readily treated. This results from the fact that the usual vascular delivery system is either occluded or non-functional, and thus tissues within affected territories cannot be properly served.

In accordance with the present invention, essential cellular substrates are delivered to beleaguered ischemic brain regions by utilizing the "back door" cerebrospinal fluid delivery route. Accordingly, the present invention provides a novel nutrient emulsion, circulatory method and system which provide necessary nutrient penetration into regions suffering vascular deprivation.

It has been found that the cerebrospinal fluid to brain relationship is not characterized by the rigid and highly selective barrier mechanism which are present at the blood-brain interface. Thus, the penetration rate of materials from cerebrospinal fluid regions to the brain relate largely to molecular size, that is, small substances penetrate deeply while large molecules move more slowly into brain substance. Although entry rates are generally inversely proportional to molecular weight, penetration is also influenced by lipid solubility and the molecular configuration of the penetrating substance. Accordingly, the present invention provides a nutrient emulsion containing essential brain nutrients including selected electrolytes, having a relatively low molecular size which, in accordance with the methods of the present invention, are caused to relatively freely diffuse from either the ventricular or subarachnoid fluid regions into the brain matter to be treated. Accordingly, the present invention provides a novel nutrient emulsion which has been purified, balanced, and perfected to fall within narrow physiologic limits while nonetheless providing the desired nutritional characteristics referred to above.

In accordance with the preferred embodiment of the present invention, this nutrient emulsion constitutes "synthetic cerebrospinal fluid" comprising preselected electrolytes, glucose, amino acids, at least one oxygen-carrying component, typically a fluorocarbon, and other components which impart to the composition a preselected pH, buffering capability, and osmolarity. This nutrient emulsion is prepared by controlling sonication time and by properly dialyzing the materials to achieve a toxic free emulsion. The resulting solution may be rapidly oxydated to $O_2$ pressures of 650 mm of mercury by using the herein disclosed modified recirculating pediatric oxygenator. As a result, a novel oxygenated nutrient emulsion is provided which is believed to exhibit exceptional therapeutic properties.

The present invention also provides a novel method and apparatus for circulating the oxygenated nutrient emulsion through cerebrospinal fluid pathways, particularly those pathways which contact brain and spinal cord tissue. According to these methods, treated tissues exhibit a substantially improved ability to resist and/or repair damage which would otherwise result from vascular occlusion. In accordance with the preferred method of the present invention, the novel oxygenated nutrient emulsion is circulated through this cerebrospinal fluid route by injecting it into brain ventricles and withdrawing it from the cisterna magna or the spinal subarachnoid space to nourish and to treat central nervous tissues. In other instances the fluid may be injected into the subarachnoid space and withdrawn from another subarachnoid position. The preferred embodiment oxygenated nutrient emulsion should be circulated to tissues to be treated in amounts sufficient to provide adequate gas exchange. Pure fluorocarbon may contain 50 ml $O_2$ per 100 ml at one atmosphere oxygen while normal blood contains only 20 ml $O_2$/100 ml under the same conditions. The oxygen carrying capability per ml of the final emulsion is considerably less than that of pure fluorocarbon by reason of its content of other constituents for normalizing osmotic pressure, buffering, electrolytes, and other physiologic balancing materials. Thus, the preferred embodiment nutrient emulsion may be charged with oxygen (100% $O_2$ at one atmosphere) to attain $pO_2$ tensions of 640–700 mm of mercury and an $O_2$ content of 20 ml per 100 ml. Under rapid circulation conditions, the integral $O_2$ exchange (fluorocarbon to tissue) has been found to be about 33%. Thus, an oxygen exchange value of about 6.6 ml $O_2$/100 ml nutrient emulsion per minute is provided by the present method.

In accordance with the preferred embodiment of the present invention, sufficient nutrient emulsion should be supplied to counteract oxygen deprivation to the affected tissue. For example, the entire supertentorial adult cat brain weighs 12 grams ($\pm 2$) and the normal metabolic consumption of oxygen of mammalian brain tissue equals 3–4 ml per 100 grams per minute. This total metabolic need may be met with the circulation rate of 6–8 mls per minute. Metabolic needs necessary to simply sustain and/or salvage tissue may be achieved by perfusion rates of one half or less of this optimum. Within these constraints an easily achieved sustenance flow rate of at least 20–30 ml/minute, optimally 45–60 ml/minute, would be anticipated to salvage 100 gms of human brain tissue. It has been found experimentally that it is possible to supply sufficient oxygen to counteract the deprivation of the affected tissue through circulation of the nutrient emulsion through the cerebrospinal fluid route. In fact, under carefully controlled conditions, it is believed within the scope of the present invention to nourish the entire human brain using the preferred embodiment apparatus, method and substance of the present invention. In this manner, central nervous neurons deprived of major blood supply may be sustained without significant damage.

In accordance with the preferred embodiment of the present invention, a novel system is disclosed for administering and maintaining the oxygenated nutrient emulsion for delivery and circulation through the cerebrospinal route.

The preferred embodiment system of the present invention effectively carries out the circulation and equilibration of the nutrient emulsion during treatment. This system, which is diagrammatically illustrated in FIG. 1, generally comprises a reservoir containing nutrient emulsion; means for delivering the nutrient emulsion at preselected flow rates; an oxygenation means for equilibrating the nutrient emulsion to desired gaseous tension levels; heat exchanger and/or cooling unit means for selectively controlling the temperature of the nutrient emulsion; filtering means for cleansing the nutrient emulsion; and circulation monitoring means for insuring that desired circulation flows and pressures are maintained within the system.

The present invention also provides a method of diagnosing conditions of neurologic tissue in mammals. This novel method generally comprises providing an artificial spinal fluid of known composition, injecting that artificial spinal fluid into at least a first portion of the cerebrospinal pathway of a mammal, withdrawing a diagnostic fluid from a second portion of that pathway to create a circulation of fluid at least through a portion of said pathway, monitoring the composition of said diagnostic fluid, and comparing for at least a selected difference in the compositions of said artificial spinal and diagnostic fluids, whereby the detected differences in those compositions are at least diagnostic of neurologic tissue disposed along said portion of the cerebrospinal pathway. In accordance with the diagnostic methods of the present invention, the diagnostic fluids may be monitored for differences in oxygen content, lactic acid concentration, carbon dioxide concentration, potassium and/or sodium ion concentration, enzyme concentration, pH difference, ammonium concentrations, GABA (gamma-aminobutyric acid) and other amino acid(s) concentrations, microorganism content, bacterial count, myelin fragments, cellular fragments or organelles, malignant cells, and/or poisons.

It is also within the scope of the present invention to provide a novel nutrient liquid and/or diagnostic liquid for treating cerebrospinal tissue containing various novel specified components which is formulated using novel methodology.

It is additionally within the scope of the present invention to provide a novel apparatus for treating patients having ischemic-hypoxic tissues, including novel injection and withdrawal means comprising a novel catheter means which is particularly adapted for injecting oxygenated nutrient liquid into a cerebral ventricle without danger of substantially damaging neurologic tissue in the vicinity of that ventricle.

In addition to the methods described above, it is within the scope of the present invention to provide additional therapeutic agents to the nutrient emulsion, such as antineoplastic agents; antibiotics, and/or other therapeutic agents for use in treating the target tissue(s).

Accordingly, the primary object of the present is the provision of a method, substance, and system for providing early stroke treatment.

Other objects of the present invention are to provide treatments for brain and spinal cord injuries, cerebral hemorrhage, cerebral vasospasm, senility, after general hypoxia and other hypoxic-ischemic related neurological disorders.

It is a further object of the present invention to provide therapeutic treatment which may sustain the life of the brain and central nervous system tissues in case of profound shock and/or temporary cardio-respiratory failure.

It is a further object of the present invention to provide life-sustaining support to the brain and/or spinal cord tissues during the conduct of neurological or cardiovascular surgery.

Other objects of the present invention are the provision of methods which may compliment treatments of central nervous system neoplasms by either external radiation and chemotherapy by providing local tissue hyperoxygenation or drugs which may enhance drug or radiation tumorocidal effects.

Further objects of the present invention include the provision of methods which are useful in treating anoxic states attending birth injury. The present method will also assist in removal of central nervous system poisons.

These and other objects of the present invention will become apparent from the following more detailed description.

BRIEF DESCRIPTION OF THE DRAWINGS

FIG. 13 is a diagrammatic view of an alternate embodiment oxygenated nutrient emulsion delivery system for use in performing the methods of the present invention.

DESCRIPTION OF THE PREFERRED EMBODIMENTS

In the following more detailed description, numerous examples have been selected for the purposes of explanation and illustration of the preferred embodiments of the present invention. One of ordinary skill in the art will recognize that various changes may be made in the materials and methods disclosed herein without departing from the scope of the present invention, which is defined more particularly in the appended claims.

Figure 1:
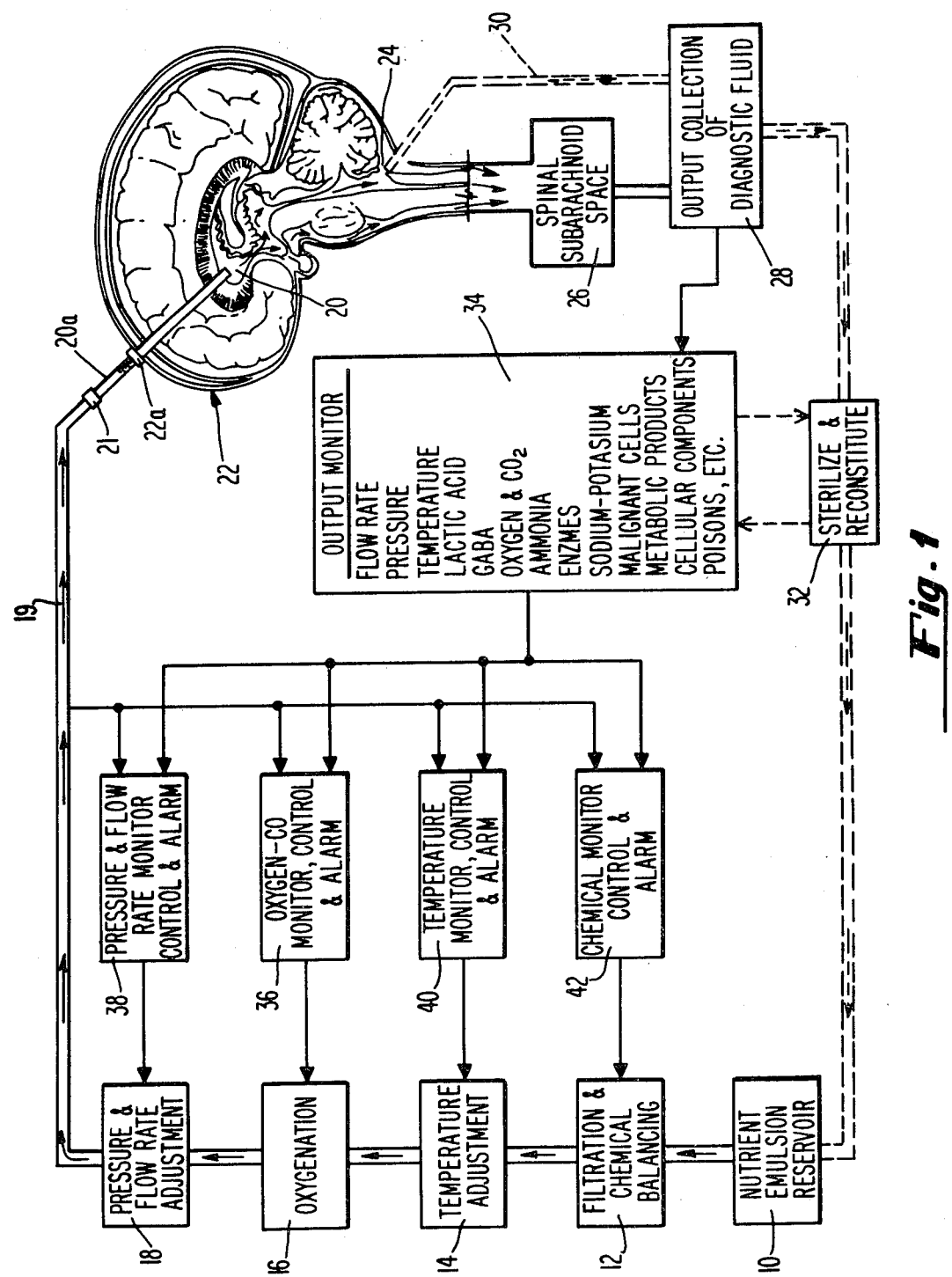
FIG. 1 is a diagrammatic view of the preferred embodiment treatment system of the present invention illustrating the circulation of nutrient emulsion from a reservoir, into a cerebral ventricle, such as a lateral ventricle, through a portion of the cerebrospinal fluid pathway for output from the spinal subarachnoid space or from the cisterna magna.

Referring now to FIG. 1, the preferred system for circulating nutrient emulsion through a cerebrospinal pathway is diagrammatically illustrated. As shown in FIG. 1, a nutrient emulsion reservoir 10 is provided for receiving and retaining nutrient emulsion, the preparation of which will be described more fully hereinafter. In accordance with the preferred system and method of the present invention, the nutrient emulsion is injected into a cerebrospinal pathway following pH adjustment and filtering, temperature adjustment, oxygenation, and adjustment of the pressure and flow rate of the nutrient input stream. In FIG. 1, these steps are illustrated diagrammatically at 12, 14, 16 and 18 respectively. Preferably, the nutrient input stream is delivered to a ventricle of the brain, and more particular to a lateral ventricle 20 of the human brain, designated generally 22. Injection of the nutrient input stream permits the oxygenated nutrient emulsion to come into contact with the subarachnoid spaces, miniature Virchow-Robins spaces, cerebral and cord surfaces, and cerebral ventricles. For the system illustrated in FIG. 1, the nutrient input stream is diagrammatically illustrated as being injected into a lateral ventricle 20. Since the lateral ventricle is in fluid communication with other portions of the cerebrospinal pathway, withdrawal of fluid from a portion of the pathway which is remote from that ventricle will create a circulation of fluid within the cerebrospinal pathway. More particularly circulation of the nutrient input stream though at least a portion of the cerebrospinal pathway may be accomplished by withdrawing fluid from the spinal subarachnoid space, diagrammatically illustrated as 26 in FIG. 1, or alternatively, from the cisterna magna 24.

It is not necessary to conduct steps 10-18 in the sequence illustrated in FIG. 1. In FIG. 13 the presently preferred apparatus for delivering oxygenated nutrient emulsion is diagrammatically illustrated. This apparatus, which may be easily constructed using a pediatric blood oxygenator such as an H-800 Pediatric Oxygenator available from The William Harvey Cardiopulmonary Division of C. R. Bard, Inc., Santa Ana, Calif. 92705, comprises a nutrient emulsion reservoir having oxygenation and temperature adjustment loops for constantly oxygenating and adjusting the temperature of the nutrient emulsion contained within the reservoir. In this manner the flow rates of nutrient emulsion provided from oxygenation by oxygenator 102 or for temperature adjustment 104 may be independently varied through adjusting the flow rate of delivery by variable speed pumps 103 or 105 to optimize the temperature and $pO_2$ characteristics of the oxygenated nutrient emulsion to be delivered for injection by variable speed delivery pumps 106 and 107. As normally used, pediatric blood oxygenators fail to provide a sufficient oxygen transfer rate to fluid flow rate to accommodate the emulsion of the present invention. The minimum blood flow rate of the H-800 oxygenator, for example, is 0.5 liters per minute, and the oxygen transfer rate (to blood) at this flow rate is less than about 25 ml/min. By routing the output 101 of the oxygenator to the reservoir, the oxygenator output pump 103 may operate at flow rates which easily achieve about 7 liters per minute of oxygen transfer to the fluorocarbon emulsion contained in the 2000 ml reservoir. At the same time, delivery pumps 106 and 107 may provide much lower flow rates of nutrient emulsion to the animal undergoing treatment. In a similar manner, heat exchange may also be optimized. In order to maintain optimal $pO_2$ values, each conduit of this system should be composed of an oxygen impermeable material to prevent leakage of oxygen from the oxygenated nutrient emulsion during processing and delivery. The filtration and chemical balancing procedures followed in preparing the nutrient emulsion are not presently performed "on line", however it is anticipated that chemical balancing may be performed as a closed loop process, as illustrated in FIG. 13. Filtration 108 is performed on line under pressure from pump 106 using a millipore bacterial filter. Pump 107 establishes the final injection rate. The flow of nutrient emulsion to the chemical balancing system is adjusted using variable speed pump 111. In the embodiment of FIG. 13, pressure monitoring and control is accomplished using an open side arm 114 bearing indicia thereon which correspond to the hydraulic pressure of oxygenated nutrient emulsion within delivery line 19. The height of the side arm is adjusted so that overflow will occur when the maximum desired intracranial pressure has been obtained.

As shown in FIG. 1 the oxygenated nutrient emulsion input stream is carried through input stream conduit 19 to an injection cannula 20a which is coupled thereto by coupling 21. Injection cannula 20a is rigidly attached to skull 22 by fitting 22a which holds the cannula in its proper orientation to permit injection of the oxygenated nutrient emulsion into lateral ventricle 20.

If preferred, a double lumen catheter, such as catheter 120 (FIG. 13), may be utilized in place of input cannula 20a. One of the lumens of this catheter should be connected to a pressure monitoring means for monitoring the intracranial pressure within the lateral ventricle 20. This pressure monitoring means may comprise an open side arm, such as side arm 122 which functions similarly to side arm 114.

The preferred injection means of the present invention comprises a cerebral catheter means for insertion into a brain ventricle. This injection means comprises means for preventing a portion of the catheter located within a brain ventricle from damaging tissues surrounding the ventricle. In the preferred embodiment, an inflatable balloon tip may be provided for this purpose. The actual injection of nutrient emulsion into the brain ventricle is accomplished by providing an arrangement of outlet holes disposed as a series of slits radially spaced around the catheter tip. Both the injection means and withdrawal means also further comprise attachment means for attaching the catheter to the body in the vicinity of the injection or withdrawal sites. Thus the injection catheter may comprise a means for fixing at least a portion thereof with respect to the skull to insure catheter stability. The withdrawal catheter, which may have a tip with multiple perforations disposed therein, further comprises means for attaching at least a portion thereof to tissue in the region of the subarachnoid space. This attachment means may include a staple for attaching a non-collapsible portion of the catheter to a lumbar region of the skin.

In many applications, the oxygenated nutrient emulsion will be delivered under normothermic conditions, that is, at about 37° C. Under these conditions, and under hypothermic or hyperthermic conditions where the delivery temperature of oxygenated nutrient emulsion is higher than ambient temperature, temperature adjustment is easily accomplished by providing a thermostatically controlled heater coupled to a suitable heat exchanger for adjusting the temperature of oxygenated nutrient emulsion recirculated to the nutrient emulsion reservoir.

Figures 2, 3:
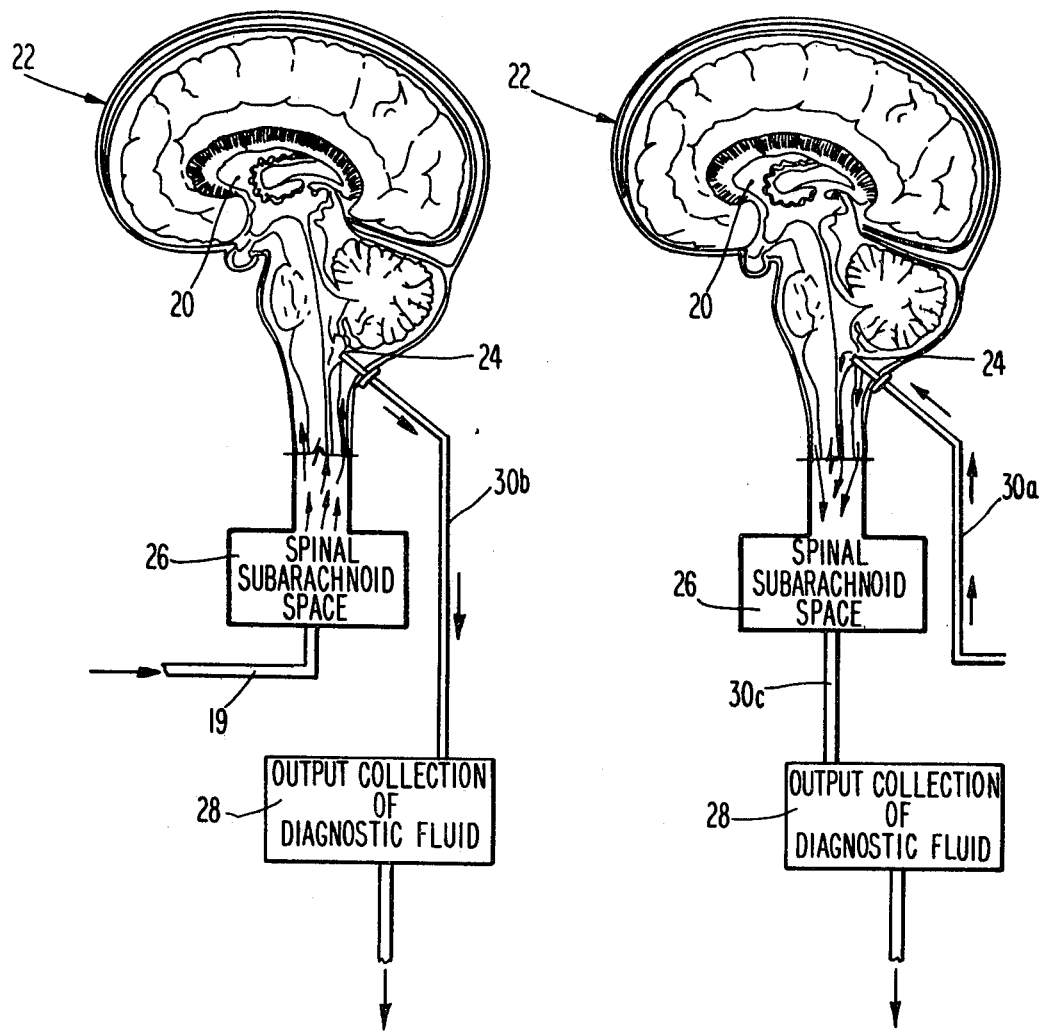
FIG. 2 is a diagrammatic view of a portion of the preferred embodiment treatment system of FIG. 1 illustrating an alternate circulation route wherein oxygenated nutrient emulsion is injected into the spinal subarachnoid space and is collected from the cisterna magna.
FIG. 3 is a diagrammatic view of portion of the preferred embodiment treatment system illustrated in FIG. 1 showing an alternate circulation route wherein oxygenated nutrient emulsion is injected into the cisterna magna for passage through the spinal subarachnoid space for withdrawal from a lumbar region.

The circulation route illustrated in FIG. 1 permits the treatment of at least cerebral tissues. It is within the scope of the present invention, however, to focus treatment on selected neural tissue areas, in which case alternative points of injection and withdrawal of fluid may be selected by the attending physician. For example, in the case of spinal cord injury, it is anticipated that the point of injection of oxygenated nutrient emulsion may be the lumbar, spinal subarachnoid space, with the point of withdrawal being the cisterna magna. While the above mentioned cerebrospinal pathway injection and withdrawal points are preferred, it is within the scope of the present invention to utilize other injection and withdrawal locations, provided a substantial circulation of fluid through the area of affected neurologic tissue is established by utilizing the selected loci. Such alternate pathways are illustrated in FIGS. 1–3. In FIG. 1, withdrawal of the nutrient emulsion from the cisterna magna is illustrated via conduit 30 in dotted outline. In FIG. 2 input conduit 19 injects oxygenated nutrient emulsion into the diagrammatically illustrated subarachnoid space 26. Withdrawal from the cisterna magna is via conduit 30b. In FIG. 3 injection into the cisterna magna is accomplished via injection catheter 30a. Withdrawal is from the diagrammatically illustrated spinal subarachnoid space 26 via withdrawal catheter 30c.

The fluid which is withdrawn from the cerebrospinal pathway will not be of identical composition to the oxygenated nutrient emulsion which is injected at the injection point. By taking advantage of differences in composition which are detected in the withdrawn fluid, which may be considered to be a diagnostic fluid, the attending physician may easily monitor the physiologic condition of the neurologic tissue which is being treated. This diagnostic fluid may also be monitored to assure that treatment is proceeding according to plan. Accordingly, fluid which is withdrawn from the cerebrospinal pathway is directed to an output collection means 28 for collecting diagnostic fluid. Preferably, an output monitor 34 will continuously monitor various chemical and physical characteristics of the diagnostic fluid for such properties as flow rate, hydraulic pressure, potassium and sodium ion concentration, temperature, lactic acid concentration, gamma amino butyric acid and other amino acid concentrations, oxygen concentration, carbon dioxide concentration, enzymes, and ammonia concentration. The output of this output monitor will not only provide the attending physician with information concerning the state of the cerebrospinal tissue being treated, but also will be fed back to the monitor, control and alarm systems for at least pressure and flow rate, temperature, oxygen-carbon dioxide and chemical constituency, as described more fully hereinafter. This diagnostic system takes advantage of the fact that ischemic neurologic tissue produces higher concentrations of such materials as Gamma-aminobutyric acid (GABA), lactate ion (lactic acid), enzymes and/or LDH (lactic dehydrogenase), ammonia, and other constituents which have been determined by analyzing cerebrospinal fluid of patients subjected by disease to similar anoxic conditions.* In accordance with the system of the present invention, however, a continuous monitoring of the state of neurologic tissue is possible, since the circulation of oxygenated nutrient emulsion will produce a continuous flushing of the affected tissue regions, and thus will result in diagnostic fluid component variations which are rapidly reflective of the physiologic state of the tissues being treated. Due to the multipoint injection-withdrawal method of the present invention, dangers which are inherent in sampling natural cerebrospinal fluid at a single location are avoided by utilizing a double venting method wherein the cerebrospinal fluid pressure is at all times carefully controlled.

*See for example, "Rapid and Sensitive Ion-Exchange Fluorimetric Measurement of G-Aminobutyric Acid in Physiological Fluids", Hare et al, *Anal. Biochem.* Vol. 101, pp. 349–355 (1980) for a preferred GABA measurement method.

It is within the scope of the present invention to sterilize and reconstitute that diagnostic fluid as shown at step 32, whereupon that reconstituted diagnostic fluid may be provided as nutrient emulsion to the nutrient emulsion reservoir 10. As shown in FIG. 1, the output monitor 34 may monitor the diagnostic fluid during the sterilization and reconstitution processes and, if desired, ensure that the reconstituted fluid satisfies the requirements of the nutrient emulsion reservoir. As shown in FIG. 1, in order to ensure that appropriate degrees of oxygenation, filtration and chemical balancing, temperature adjustment, and pressure and flow rate are maintained, the nutrient input stream is monitored by various monitors, controls, and alarms, which are intended to provide a fail-safe nutrient input stream. In particular, a pressure and flow rate monitor, control and alarm 38 is provided for monitoring the pressure and flow rate of the nutrient input stream, for controlling the pressure and flow rate adjustment 18 to establish desired pressures and flow rates, and for sounding an alarm in the event that the nutrient input stream exceeds or falls below preselected pressures or flow rates. If desired, this alarm may additionally disable the pumping mechanism producing flow of the nutrient input stream such that the unit "shuts down" upon detection of unacceptable input stream conditions.

Referring now to the temperature monitor, control and alarm, the temperature characteristics of the nutrient input stream are similarly detected, at least to ensure that hyperthermic states, except when used as therapeutic modality, are avoided. While in most instances, the nutrient input stream will be adjusted to a 37° C. temperature, it may be desired to select hypothermic temperatures in order to establish certain treatment conditions. In either event, the temperature monitor will continuously detect the temperature of the input stream, will control the temperature adjustment 14 to establish a preselected temperature, and will sound an alarm and/or disable the system in the event that a preselected temperature range is not maintained in the nutrient input stream.

Referring now to the chemical monitor, control and alarm 42, the nutrient input stream will be continuously monitored for one or more chemical or physical characteristics of the nutrient input stream, and will control the chemical balancing, filtration, etc. which is performed by the filtration and chemical balancing unit 12. The chemical monitor, control and alarm may, for example, monitor the pH, osmolarity, electrolyte component, carbohydrate component, amino acid component, or other components of the nutrient emulsion to ensure that the nutrient input stream falls within preselected stream characteristics. In the event that these characteristics do not fall within the preselected range, the alarm for unit 42 may sound and/or may disable the system to thereby prevent further injection of nutrient input stream into the cerebrospinal pathway.

Finally, an oxygen/carbon dioxide monitor, control and alarm unit 36 is provided which continuously monitors the oxygen and carbon dioxide contents of the nutrient input stream, which controls the oxygenation unit 16, and which sounds an alarm in the event that the oxygen or carbon dioxide concentrations do not fall within preselected ranges. It is anticipated that each of units 36-42 may provide continuous displays of the information monitored from the nutrient input stream, and may, if desired, enable back-up units which either manually or automatically supplement or replace the functions of units 12-18 in the event that those units are not functioning to produce a nutrient input stream within the desired ranges. For example, it is anticipated that a manual or battery operated pump, oxygenator, filter, and pressure and flow rate adjustments be provided to enable emergency operation of the system, since continual nutrient flow is lifesaving for the devitalized portion of the treated organ.

The preferred nutrient emulsion of the present invention is comprised of carefully formulated components which, to the extent possible while maintaining desired therapeutic activity, mimic the physical and chemical characteristics of natural cerebrospinal fluid. Generally, tissues and cells will not fair well if exposed to large volumes of non-physiologic ionic solutions. Accordingly, it has been recognized that appropriate electrolyte compositions at the tissue level are indispensable when it is considered that the circulatory method of the present invention would otherwise result in the washing and the dilution of electrolytes from the region even after short terms of circulation, to the detriment of cell membrane functions. Accordingly, in accordance with the preferred embodiment of the present invention, sodium, potassium, calcium, magnesium, and chloride ions are carefully balanced in the nutrient emulsion of the present invention to thereby create, to the degree possible, normal extra-cellular compositions. The present invention also provides a non-aqueous oxygen transfer component for selectively combining with oxygen and for transferring oxygen to the tissues to be treated. Numerous compounds are known to the art which are characterized by having a high solvent property for oxygen, carbon dioxide, and other gases. The preferred non-aqueous oxygen transfer component of the preferred nutrient liquid should exhibit when so charged, oxygen vapor pressure ranges of above 400, and preferably 600, Torr. Such oxygen transfer components should similarly not have in themselves high vapor pressures which would boil at body temperatures, nor have viscosities which are difficult if not impossible to emulsify. Generally, the preferred compounds for use as non-aqueous oxygen transfer components are fluorocarbon polymers, such as perfluorocarbons, perfluorinated alkyl polyethers, fluoroethers, fluoramines, etc. While compounds within these groups range in molecular weight from 250 to 7000, their selection for use as non-aqueous transport components are based upon the combination of features of the proper vapor pressure, molecular weight, viscosity, and emulsifiability, emulsion stability and tissue distribution. One such fluorocarbon which has been found to be particularly suited for the non-aqueous oxygen transport component of the preferred nutrient liquid is a reagent grade perfluorobutyltetrahydrofuran which has been sold by the 3-M Corporation under the trademark "FC-80". FC-80 has an oxygen solubility coefficient $ScO_2$ of 0.45 of ml $O_2$/ml at $pO_2$ of 760 Torr. See Navari et al., *Res. Exp. Med.* 170, pp. 169-180 (1977), which paper is specifically incorporated by reference as if fully set forth herein. It should be noted that whole blood under the same circumstances contains 0.23 ml $O_2$/ml. The FC-80 $ScO_2$ is linear from 760 to 200 Torr but declines quite rapidly below the lower level. The high oxygen diffusion coefficient ($5.71 \times 10^{-5}$ cm$^2$/sec per second) indicates more than adequate FC-gas in a physiologic sense. Similar studies concerning $CO_2$ solubility and diffusion indicate that absorption and release are described by a straight line function. From these observations, metabolic tissue $CO_2$ accumulations should theoretically be easily removed by fluorocarbon solutions administered through a circulatory method.

Not only do fluorocarbons possess these unique physical gaseous properties but they are for the most part non-toxic. The main acute toxicity has been found to reside in free fluoride ion accumulation which occurs mainly from sonication. See, Clark et al., *Fed. Proc.* 34, pp. 1468-1477 (1979). The free ion can, however, be removed by repetitive dialysis and the emulsion thereby rendered physiologically acceptable. Accordingly, the preferred embodiment nutrient liquid of the present invention, which has been dialysized and filtered through a millipore filter, has evidenced no toxicity either in short term or long term use during circulation through cerebrospinal pathways of animals. One chief advantage of the CSF circulation route is that most or all the nutrient liquid can be removed by washing at the time of treatment termination. In this way long term cellular retention as previously noted for liver and reticuloendothelial cells in vascular circulations of oxygenating liquids may be avoided.

In the preferred embodiment nutrient liquid of the present invention, an emulsification component is provided for permitting the emulsification of the nutrient component with the oxygen transfer component of that liquid. See Clark et al, *Triangle II*, pp. 115-122 (1972b); Clark et al, *Microvasc. Res.* 8, pp. 320-340 (1974). The best currently available material for this purpose is believed to be block polymer polyols, which are known to the art as "pluronics", of which, pluronic F68 has proven to be a most efficient emulsifying agent. As used in a nutrient liquid as described more fully hereinafter, the toxicity from such a pluronic detergent is negligible. At the present time, however, it is anticipated that other emulsification components which will permit the non-aqueous transfer component of the nutrient liquid to become soluble with respect to the aqueous nutrient component of the nutrient liquid may be utilized to provide solutions which have adequate physiologic perimeters. Such other means of solubilizing fluorocarbons includes the formation of micelles, etc.

In the preparation of the preferred nutrient liquid, an important factor in producing an acceptable nutrient liquid is the achievement of an acceptable final osmotic pressure. The osmotic pressure of the nutrient liquid will depend upon the amount of the emulsification component, the particle size of the fluorocarbon, and the ionic composition of the aqueous nutrient component. In accordance with the preferred method of preparing the nutrient liquid of the present invention, toxic emulsification components should be removed by dialysis.

Fluorocarbon particle size will be controlled by sonification time and filtering, while the ionic composition of the aqueous nutrient component will be carefully adjusted to produce a nutrient liquid possessing desired osmotic characteristics. If desired, a final osmotic tuning may be accomplished in accordance with the method of the present invention by adding ascorbic acid to the nutrient liquid.

In order to provide fully successful treatment of ischemic tissues, it is desirable to provide nutrient liquid for circulation around those tissues which will compensate for relative or complete deficiencies of blood transport metabolites. In addition to oxygen, other tissue metabolic requirements include glucose, amino acids, ions, hormones, vitamins, etc. While in temporary treatment conditions, it may be suitable to temporarily omit one or more vitamin, hormone, ion, or amino acid, for prolonged treatment and to produce the most desirable results, it is preferred to provide substantially all of the above mentioned metabolites in the preferred nutrient liquid. It is at least desirable to provide in the nutrient liquid all components necessary to support aerobic metabolism which will be available within the medium for use at cellular levels. Glucose deprivation of central nervous system tissue causes a serious cellular metabolic deficiency, as does the same degree of oxygen deficiency. Accordingly, by providing a total and finely adjusted mixture that has all the necessary components for total cell survival, an extremely efficient and therapeutic liquid material is provided which is ideal for circulation through the cerebrospinal pathways.

In order to illustrate the preferred method and composition of such an oxygen-nutrient material, the following example is provided.

EXAMPLE 1

Under conditions of replacing blood borne materials by perfusion all nutrients necessary for aerobic metabolism must be available within the medium for immediate use at cellular levels. As far as the central nervous system is concerned, glucose deprivation causes as serious a cellular metabolic deficiency as does the equivalency of oxygen lack. To achieve the desired ends all known essential nutrients have been added to the FC (fluorocarbon) emulsion. FC itself thereby serves the purpose of a gas transport system while the aqueous emulsion phase contains an array of cellular metabolic essentials. The total and finally adjusted mixture has all the necessary ingredients for total cell survival. The combination material is referred to as an oxygen-nutrient formula (Ox-N), or oxygenated nutrient emulsion.

| Method and Composition Preparation of Oxygen-Nutrient Material | | |
|---|---|---|
| 1. Reagents | | |
| (A) | 5% Commercial grade Pluronic F68 (Basic Wynadotte). | |
| (B) | 20% W/V FC-80 (3M Corporation) | |
| (C) | Synthetic C.S.F. | |
| | Sodium Chloride | 7.3 gm/L |
| | Potassium Chloride | 300 mg/L |
| | Calcium Chloride (dehyd) | 200 mg/L |
| | Magnesium Sulfate | 300 mg/L |
| | Sodium Phosphate (hepta) | 200 mg/L |
| | Sodium Bicarbonate | 190 mg/L |
| | Adjust the pH to between 7.380–7.420 with 10% Ascorbic Acid | |
| (D) | Bacitracin Inj. 50,000 U/vial (Pharmacy) reconstitute with 10 ml saline to give a concentration of 5000 U/ml. Use 0.2 ml for each liter of perfusate to obtain a concentration of 1,000 units per liter of perfusate. | |
| (E) | Essential Amino Acids (Pool) (Sigma) | |
| | D-Glutamic Acid | 11.8 mg |
| | L-Glutamine | 730.0 mg |
| | DL-Serine | 26.3 mg |
| | D-Threonine | 30.0 mg |
| | D-Lysine | 38.8 mg |
| | D-Valine (optional) | 19.0 mg |
| | D-Leucine | 14.0 mg |
| | DL-Isoleucine | 13.0 mg |
| | D-Phenylalanine | 15.0 mg |
| | DL-Tyrosine | 14.0 mg |
| | D-Methionine | 4.5 mg |
| | Before oxygenating the fluorocarbon emulsion add 9.8* mg. amino acid and 200 mg dextrose for each 100 ml of emulsion. | |
| (F) | Steroid (Methylprednisolone sodium succinate) 125 mgs. (The Upjohn Company). Reconstitute the steroid with 2 ml of diluent to obtain a concentration of 62.5 mg/ml. Add 0.5 ml of this mixture to each liter of emulsion before oxygenation (31.2 mg/L). | |
| (G) | 1 N NaOH | |
| 2. Materials | | |
| (A) | Sonifier Cell disrupter (Branson) Model W185D | |
| (B) | Waring Blender for mechanical dispension of Pluronic Acid. | |
| (C) | Dialyzer tubing ⅞ in. (22 mm) (Thomas). It is necessary to dialize the emulsion to remove fluoride ions as well as other low molecular weight contaminants. | |
| (D) | Whitman Filter Paper #1 (46 × 57) (Thomas). The emulsion should be filtered to remove particles originating from disrupted carbon skeletons of flurocarbon during sonication. | |
| (E) | 0.8 micron filter unit (Thomas). Sterilization is accomplished by filtering the emulsion through a micro filter. | |
| (F) | $CO_2$ tank (Welders Supply Company) $CO_2$ is used as a defoaming agent while sonicating. | |
| (G) | 100% $O_2$ tank (Welders Supply Company) $CO_2$ is used as a defoaming agent while sonicating. | |
| (H) | 100% $O_2$ tank (Welders Supply Company) for saturating perfusate. | |
| (I) | Sterile Culture Flasks (Thomas) for storing perfusate. | |
| (J) | Gas Dispersion Tubes (Fisher Scientific Company) for equilibrating the emulsion with $O_2$. | |
| (K) | Aspiratory Bottle (Thomas) | |
| | a. 250 ml capacity-cut off 2½″ from the neck with a glass cutter in order to accommodate the macrotip for sonification. | |
| | b. 500 ml capacity - for equilibration of the emulsion with 100 ml capacity - 100% $O_2$. | |
| (L) | K50 Extension tubing. Capacity approximately 2.1 ml length 40.7 centimeters (20 in.). | |
| (M) | Circulating Pump | |
| (N) | Sonification Assembly | |
| | a. Fill a container with crushed ice; one that will allow drainage of the water as the ice melts (a fish tank will do). | |
| | b. On the serrated outlet near the bottom of the aspiratory bottle connect seven lengths (140 in.) of K50 extension tubing. Place the bottle in the ice bath and connect the tubing to circulating pump. | |
| | c. Place the precooled Pluronic acid in the aspirator bottle. Drape and return extension tubing from the pump | |

| -continued |  |
|---|---|
| Method and Composition Preparation of Oxygen-Nutrient Material | |
| | over the side of the bottle. Drape the tubes from the $CO_2$ tank over the side of the bottle and bubble slowly. Carefully lower the macrotip into the solution and start sonification. |
| 3. Method 20% FC-80 (5% Pluronic (F68)) (w/v) | |
| (A) | Place 25 gms of F68 + 250 ml of artificial CSF in a Waring blender and blend at a high speed for 2 minutes. The solution will become very foamy. For best results the solution should be refrigerated overnight before using. This allows the head of foam to settle and precools the solution to the proper temperature for sonification. |
| (B) | Place the precooled Pluronic acid solution in the aspirator bottle. Turn on Sonifier. With a Pasteur pipette add 58.8 mls (100 gm) of FC-80 over a 30 minute period sonifying throughout. Once added allow the mixture to sonicate for 45 minutes. Be sure that the temperature does not exceed 20° C. |
| (C) | Cut dialyzer tubing that has been pre-soaked in artificial C.S.F. into 60-inch strips. Fill each strip half full with the mixture. Place strips in containers filled with approximately 1000 ml, of artificial C.S.F. Refrigerate and allow to dialize for 48 hours. The dialyzing solution should be changed every twelve hours, and the emulsion checked and transferred to additional tubing since the volume is considerably increased during dialysis. |
| (D) | After dialysis filter the solution through Whitman #1 filter paper, then take the total volume. 25 gm of Pluronic acid and 58 750 ml of emulsion. The former volume represents 20% FC-80 and 5% F68 w/v ratio. The emulsion should be kept in an ice bath while processing. |
| (E) | Add bacitracin to the emulsion. The pH at this point should be between 6.5 and 6.8. |
| (F) | It is necessary to adjust the electrolytes at this stage.<br>Unadjusted electrolytes:<br>Na = 127<br>K = 5<br>Cl = 126<br>$CO_2$ = 1.5<br>Osmolarity = 271<br>It is necessary to add 696 mg Na Cl/L of emulsion in order to normalize the electrolytes.<br>Adjusted electrolytes:<br>Na = 131<br>K = 3.8<br>Cl = 130<br>$CO_2$ = 3<br>Osmolarity = 303 |
| (G) | Using 1.0 N NaOH adjust the pH to between 7.380 and 7.420, then check the osmolarity (Range 298-317) |
| (H) | Sterilize the emulsion by filtering through 0.8 micron filter. The emulsion can be frozen at −20° C. and is stable for several months. |
| 4. Immediately Before Using Emulsion | |
| (A) | Add: Glucose 0.8-2.5 gm/L<br>Amino Acid 0.098 gm/L<br>Steroid 31.2 mg/L (optional) |
| (B) | Warm the emulsion to 37° C. and equilibrate with 100% $O_2$ using a gas dispersion tube for 30 minutes to obtain a $pO_2$ of between 580-660. |
| (C) | A typical batch of FC-80 emulsion shows the following properties:<br>Na = 131 meq/L<br>K = 3.8 meq/L<br>Cl = 130 meq/L<br>$CO_2$ = 3 meq/L<br>Glucose = 186 mg. %<br>Osmolarity = 311 mOsM |
| (D) | A typical batch of oxygenated nutrient emulsion contains:<br>Fluorocarbon = 78.6 ml/L<br>Pluronic Acid = 213 ml/L<br>Na Cl = 7.3 gm/L<br>Potassium Cl = 300 mg/L<br>Calcium Cl = 200 mg/L (dehydrated)<br>Mg Sulfate = 300 mg/L<br>Sodium Phosphate = 200 mg/L<br>Sodium Bicarbonate = 190 mg/L<br>Amino Acid Pool = 0.098 gm/L (added to fluorocarbon)<br>Manitol Injection = 50 ml/L USP 259<br>Bacitracin = 5000 units/L<br>Gentamicin = 80 mg/L<br>Dextrose = 2 gm/L<br>Ascorbic Acid = 0.5 ml/L (10%)<br>Sterile Water = remainder per liter |

| Gas Characteristics After Oxygen Equilibration | | |
|---|---|---|
| | Unsaturated | Saturated |
| pH | 7.231 | 7.342 |
| $pCO_2$ | 3.7 | 5.7 |
| $pO_2$ | 190 | 640-5 |

*Siegel et al., Basic Neurochemistry (2nd edition), Little, Brown and Company, Boston, p. 297.

In order to provide an indication of the efficacy of the preferred treatment methods, the following examples are provided:

EXAMPLE 2

For reasons of simplicity and reproducability a model continually in use in applicant's laboratory has been employed. Osterholm, J. L., *Pathophysiology of Spinal Cord Injury*, C. C. Thomas, Springfield, Ill. (1978). Extensive experience with spinal cord injury in terms of standardization, quantitative histological studies, regional blood flow and biochemical parameters suggested these procedures. A primary pathophysiologic event in that model has been determined to be discrete regional ischemia. A microcirculatory flow failure within the injured region has been documented by many study techniques including microangiography, distribution of intravascular particulate materials, hydrogen-platinum flow studies, regional istopic techniques and lactate accumulation. Recent C 14 antipyrine microregional blood flow studies conducted in applicant's laboratory have accurately delineated the magnitude of ischemia in the injured cord. Within one hour the regional grey matter flow drops from the control of 44 cc/100 gm/min to only 2 cc/100 gm/min. The white matter is also ischemic. Blood flows in these regions are depressed from 15 cc/100 gm/min to 1-2 cc/100 gm/min.

From these observations, standarized spinal cord injury causes a restricted ischemic lesion which can be easily studied and quantitated. In this rigid system therapeutic treatment effects are readily detected by comparison with our extensive untreated injury data. It should be noted here that the mechanical injury forces used in these experiments are substantially above saturation and all wounded animals are rendered permanently paraplegic.

Circulation Experiments

Experiments were carried out by continuously injecting either saline or Ox-N emulsion saturated with $O_2$ at 1 atm into the distal subarachnoid spinal space. The outflow (withdrawal) of the diagnostic fluid was at the cisterna magna. Infusions were begun immediately after severe wounding. An infusion rate of 3 ml/minute was easily achieved, and this rate was maintained for two hours.

Oxygen

Prior to lumbar spinal infusion we were able to develop $pO_2$ tensions of $535 \pm 89$ mm $O_2$ in the Ox-N emulsion by simply bubbling 100% oxygen through the solution. Upon exit at the cisterna magna after traversing the entire spinal subarachnoid space the $pO_2$ had fallen to $243 \pm 63$. The oxygen difference between entering and exit was $292 \pm 63$, or a 55% decline, which is statistically significant at the $P < 0.001$ level. This finding indicates a rapid $pO_2$ exchange during the thirty seconds or less transit time. For various technical reasons our initial $pO_2$ was lower than can be achieved under idealized circumstances. More recently it has been possible to regularly attain $pO_2$ of about 650 Torr. Even better experimental results might have now been obtained under conditions of higher $O_2$ tension.

Carbon Dioxide

FC-80 is an efficient $CO_2$ exchange and transport agent, and the emulsion therefore easily extracts tissue $CO_2$. This is indicated by an initial emulsion $pCO_2$ of 2.7 Torr which rose to 16.0 Torr after the tissue perfusion contact. This represents a 593% increase in FC-80 $CO_2$ ($P < 0.001$). The emulsion also removes other acid metabolites since in some experiments the inherent buffering capacities were exceeded as the exit fluid pH exhibited a considerable depression toward the acid side (original pH 7.4, exit pH 7.0). This pH change exceeded any acid contribution by the collected $CO_2$, and amounted to 0.248 mole lactate/hour.

A. Cross Sectional Area (Edema)

Frozen tissues were sectioned and stained (H & E, and acid phosphatase). The sections were evaluated by projection to 25× magnification and preselected lesion parameters measured by means of a compensating polar planimeter. There was considerable increase in the untreated injury cord cross sectional area (1280 mm²) which was significantly reduced in the Ox-N experiments, (896 mm²). We have assumed that this substantial cross sectional cord area increase is caused by edema fluid. In the course of other experiments, the degree of edema appearance has been quantified. It was found that net water accumulation at those post injury times ranged from 25% to 40%. The absolute reduction in cross sectional area by the Ox-N treatment is significant at the $P = 0.001$ level.

Lesion Size

Using our standard sampling methodology which includes skip serial sections throughout the injury region, and analysis by quantification techniques, the degree of injury induced hemorrhagic necrosis can be determined. With the perfected injury system the lesion size at any time point can be reliably predicted. The effects of saline and Ox-N circulations upon lesion size were compared to each other and to our established untreated values. The results are summarized in Table I:

TABLE I

| | LESION SIZE 2 Hour Injuries | | |
|---|---|---|---|
| | % Grey | % White | % Total |
| Standard Injury (No Infusion) | 79.5 ± 16% SD | 30.1 ± 9% SD | 39.5 ± 10% SD |
| Saline Circulation | 78.3 ± 15% SD | 25.0 ± 14% SD | 34.4 ± 12% SD |
| Ox-N Circulation | 47.4* ± 17% SD | 12.8* ± 2% SD | 19.2* ± 10% SD |

Table I - Percentages are expressed in terms of total tissue area lesioned by hemorrhagic necrosis for grey, white or total cord area two hours after severe injury with the various treatments. (*Statistical Significance $P = <0.01$. The saline values are not significant).

The data indicates a highly significant degree of protection against injury lesions afforded by the Ox-N circulation treatments. The actual lesions are halved by the treatment and this remarkable stabilizing effect upon the important white matter tracts would be anticipated to substantially improve the final functional result attending severe spinal cord injury.

Anterior Horn Cells

A technique of counting the anterior horn cells which contain visible acid phosphatase histomchemical reaction product has been developed in this laboratory. The procedure has been previously used to assess ischemic cellular effects in terms of cellular survival and/or lysis time.

From Table II it can be seen that untreated injury has a highly lethal effect upon anterior horn neurones. Within the two hour experimental time period, more than 97% of all cells at the injury center undergo cytoplasic lysis. Ox-N infusions stabilized the injured cells as 60% of all neurones were protected from lysis.

TABLE II

| ANTERIOR HORN CELLS | |
|---|---|
| Control | 34 ± 2 (SD) |
| Injury | 2 ± 1.73* |
| Injury + Ox-N circulation | 21 ± 5.12** |

Table II - Number of anterior horn cells containing acid phosphatase reaction product within well defined cytoplasmic borders, (*statistical difference from control $P < 0.001$, **Difference from injury alone $P < 0.001$).

Spinal Cord Adenosine Triphosphate (ATP)

Biochemical ATP tissue determinations were undertaken to determine the metabolic oxidative state of injured spinal tissues. This metabolite was selected for study since it reflects the progress of normal oxidative metabolism. ATP levels fall very rapidly under sufficient hypoxic-ischemic conditions. Untreated injured cords have a 200% ATP decline in one minute. In the current experiments ATP levels would be expected to reflect (1) the cellular oxidative capability and (2) functional cellular viability. The latter aspect is especially important in terms of cellular integrity which was discussed in the preceeding section.

From Table III it can be seen that 2 hour injury causes a four and three fold drop in grey matter and white matter ATP respectively. This information amply supports other observations about the degree of regional cord tissue ischemia after impaction. ATP was found in significantly higher concentration in the Ox-N experiments than noted after saline circulation alone. The high energy compound suffered only a 30% fall from normal in the oxygenated perfusion group which contrasts vividly with the 300-400% loss found with the saline treatments.

TABLE III

| ATP LEVELS ($\mu$ mol/gm) (2 hours post injury) | | | |
|---|---|---|---|
| | Injury & Saline | Injury & Ox-N | Control |
| Grey Matter | 0.46 | 1.24* | 1.88 |
| White Matter | 0.40 | 0.87* | 1.23 |

Table III - ATP tissue levels in control, saline and Ox-N injured cords. The difference between saline and Ox-N is significant *(P = 0.05). Although not shown in the Table, the Ox-N treatments also statistically increase ATP in spinal cord regions directly above (P < 0.001) the injury site.

Comparison of the above results to those later reported by R. E. Hanseabout, R. H. C. Van Der Jagt, S. S. Sohal, and J. R. Little, *Journal of Neurosurgery* 55, pp. 725-732 (1981) is of interest. Hanseabout et al report the use of a commercial oxygenated fluorocarbon artificial blood perfusate to treat experimental spinal cord injuries. Treated dogs are reported as showing improved motor function more rapidly and as having a better final hind limb functional result than did controls. To some extent, this non-prior art report confirms the spinal cord injury findings reported here.

EXAMPLE 3

Cerebrovascular Ischemia

Initial studies have been conducted to determine the efficiency of Ox-N emulsions in protecting the brain against profound ischemia. We employed the cat brain and utilized right hemispheric regional vascular interruption so that the left cerebral hemisphere might serve as an internal control. The middle cerebral artery of cat is accessible through the bony orbit. It lies immediately above the optic nerve after the canal has been opened and can be identified with certainty in that position. Preliminary experiments determined that an inconstant cerebral field was devascularized by occluding the middle cerebral artery. It became apparent that collateral blood flow via the anterior and posterior cerebral arteries supplied some retrograde filling into the experimental region. This phenomenon could be largely prevented by concommittantly reducing the mean systemic blood pressure to 70 mmHg by external bleeding. Hemorrhagic hypotension plus middle cerebral artery occulsion yielded a reasonably constant ischemic cerebral lesion from animal to animal.

In that model either saline or Ox-N were circulated from the right cerebral ventricle to the cisterna magna at a rate of 3 ml/min. Cerebral tissues were harvested one hour after vascular occlusion by immediate immersion in liquid Freon. The tissues were sectioned in the frozen state and reacted with luciferin upon photographic film. A combination of high energy cellular metabolites plus luciferin react to emit visible light, which is recorded upon the film. Tissues removed from saline treated ischemic cerebral regions were uniquely devoid of phospholuminescence, while the opposite hemisphere demonstrated this reaction to a degree similiar to that found in normal animals. Middle cerebral ischemic tissue samples from Ox-N treated animals contained sufficient high energy materials to demonstrate a positive histochemical high energy reaction one hour after vascular arrest.

EXAMPLE 4

Profound Spinal Cord Ischemia

The combined evidence from spinal cord injury and middle cerebral artery occlusion models demonstrate that the preferred oxygenated nutrient emulsion can be circulated to maintain cellular integrity and aerobic metabolism under the stress of profound regional ischemia. A third model was utilized to determine if vascular deprived neurones perfused via cerebrospinal fluid pathways with oxygenated-nutrient would continue to perform a physiologic function. A transthoracic aortic ligation just distal to the left subclavian effectively devascularizes the cervical, thoracic and lumbar cat spinal cord. In some examples the lower brain stem was also found ischemic by regional flow studies. The mid and lower thoracic cord are universally and profoundly blood deprived by this vascular interruption. Animals under light Ketamine anesthesia were treated by circulating from the lumbar subarachnoid space to the cisterna magna with either saline or Ox-N solutions. Respiratory movements were evaluated in these experiments. The lungs were ventilated by positive presence respiration, but the mechanical movements are easily distinguished from neuromuscular respiratory contractions. This is especially so since for the most part the respiration and neuromuscular drive occur at separate times and are largely asynchronous. Following the aorta ligation all physiologic neuromuscular respiratory movements progressively diminished to total cessation after 5-10 minutes in the saline treated cats. The arrest obtains for intercostal muscles as well as diaphragmatic contractions. The Ox-N treated animals, on the other hand, continue to respire in an essentially normal neuromuscular sequence. The respiration, under those conditions, were often of irregular rates, diminished in amplitude, and showed some individual magnitude variations. The singular difference between saline and Ox-N circulations is the universal persistence of respiration in the latter group. It is also true that Ox-N sustained sufficient chest bellow movements so that if the chest were closed the respirations were clinically adequate to support life.

EXAMPLE 5

Experiments have also been conducted to determine the efficacy of the herein disclosed methods on global cerebral ischemia induced in cats.

Although the Ox-N emulsions of the present invention are oxygenatable by bubbling gas through them, perfusate from stroke animals were initially found to have oxygen pressures ($pO_2$) below those known efficient oxygen exchange values ($pO_2$ less than 200) for the fluorocarbon component of the material. See Navari et al, supra. Accordingly, the pump oxygenation system described above in connection with FIG. 13 was developed to optimize fluorocarbon $O_2$ saturation. As mentioned above, this system comprises a heat exchange-oxygenator which was coupled to recirculating, warming and delivery pumps. This system rapidly oxygenates the emulsion ($pO_2 = 645$[mean] Torr) at 37° C. with oxygen gas delivered at 7 L/min.

Global cerebral ischemia experiments were conducted on cats after brevital induction and nitrous oxide oxygen (70-30%) anesthesia. A double lumen inflow cannula of the type described above was sterotactically placed into a lateral cerebral ventricle while an exit cannula was inserted either into the cisterna magna or lumbar theca. When the conduits are properly installed, the CSF pathways have little resistance and a mean flow perfursion rate of 6.0 cc/min. can be achieved through the animals without intracranial pressure alterations. Entry and exit fluid were collected for metabolic studies. Both gases were normalized by respiratory adjustment. Further experimental manipulations awaited electroencephalograph (EEG) normalization. Cerebral ischemia was produced by the combined insult of hemorrhagic hypotension (mean arterial blood pressure lowered to 30±3 mm Hg) plus simultaneous carotid artery clamping. This method caused a bihemispheric isoelectric EEG within 5-8 minutes. After sustained and total cerebral electro silience for 15 minutes, the carotid arteries were unclamped and the withdrawn blood reinfused.

A well accepted measure of cerebral function, the EEG, was used to assess both the degree of insult and subsequent discovery. A computer based EEG method, compressed spectral analysis, was used to determine brain activity. A Nicolet Instrument Corporation "MED-80" computer utilizing frequency analysis package "Super C" was used with the following setup parameters:

2 channels, 1024 SEC. EPOCH, 1024/PTS.EPOCH
2 sweep average/printout.

The total output is expressed in (microvolts$^2$) assuming a constant source impedence of 1 ohm. The data presented here is the total cerebral power 0.3-25 Hz in picowatts. Recordings were made from skull electrodes at maximum sensitivity of 1 picowatt. Since a steady state prestroke EEG was obtained, each animal served as its own control.

Figure 4:
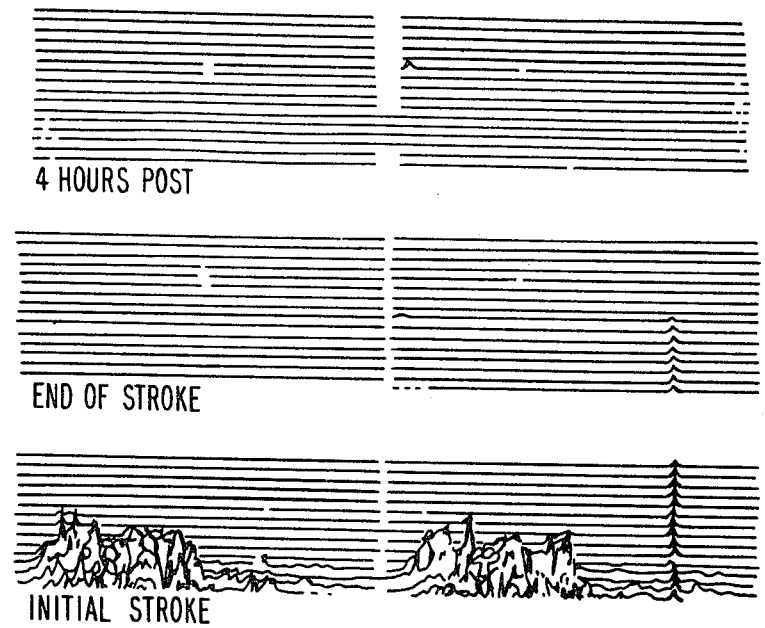
FIG. 4 is an EEG power recording from the left and right hemispheres of a cat showing traces from the time of an initial stroke, at the end of the stroke, and four hours after the stroke.

Ten animals had cannulas placed and the stroke accomplished without perfusion. A second control group of ten animals were treated similarly, but were also perfused through the ventriculo spinal (lumbar) route with nutrient solution without fluorocarbon. There were no apparent differences found for post-stroke electroencephalographic activity in these groups. As a measure of stroke severity, 13 animals (of 20) had persisting electrocerebral silience. Of the remaining animals, 5 gained only 2% of their base line power while two had 10% power return within the 4 hour experimental period. FIG. 4 is a representative EEG power tracing from the left and right cerebral hemispheres of a cat perfused only with nutrient solution without fluorocarbon and which exhibited persisting electro-cerebral silience during the 4 hour experimental period. The tracings are read from bottom upwards. Normal activity is seen in the lowest tracing and is totally arrested by the ischemic insult half way through the first grouping. There is electro-cerebral silience thereafter througout the experimental period.

Figure 5:
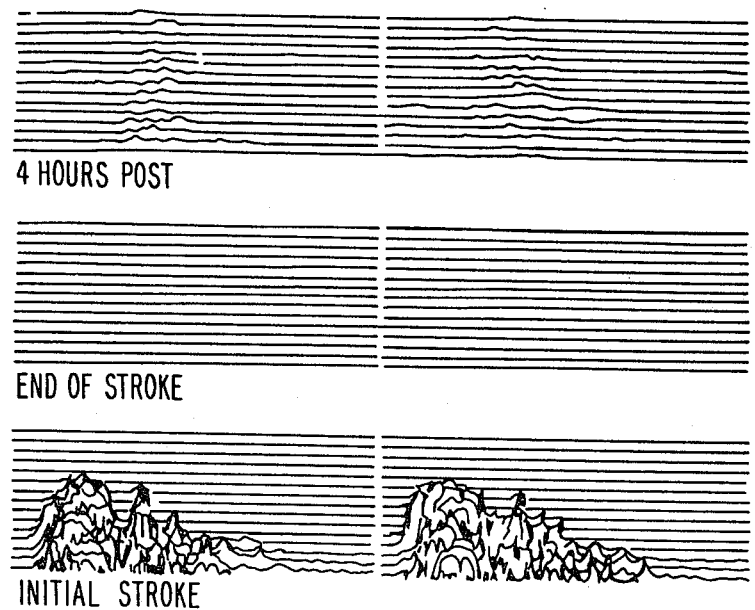
FIG. 5 is an EEG recording of an animal perfused with oxygenated nutrient emulsion having a $pO_2$ level of 400 and showing a 5% return of EEG at 4 hours.

Thirteen cats underwent the same experimental procedure, but were perfused immediately after ischemia with bubble oxygenated nutrient solution (pO$_2$=400). For these cats, the flow rate was 4 ml/min with withdrawal from the umbar theca. Five exhibited continued electro-silience whereas 8 demonstrated EEG recovery from 5% (6 animals) up to 34% (2 animals). FIG. 5 is a representative EEG tracing of one of the eight animals demonstrating 5% recovery after perfusion with oxygenated nutrient emulsion (pO$_2$=400).

Figure 6:
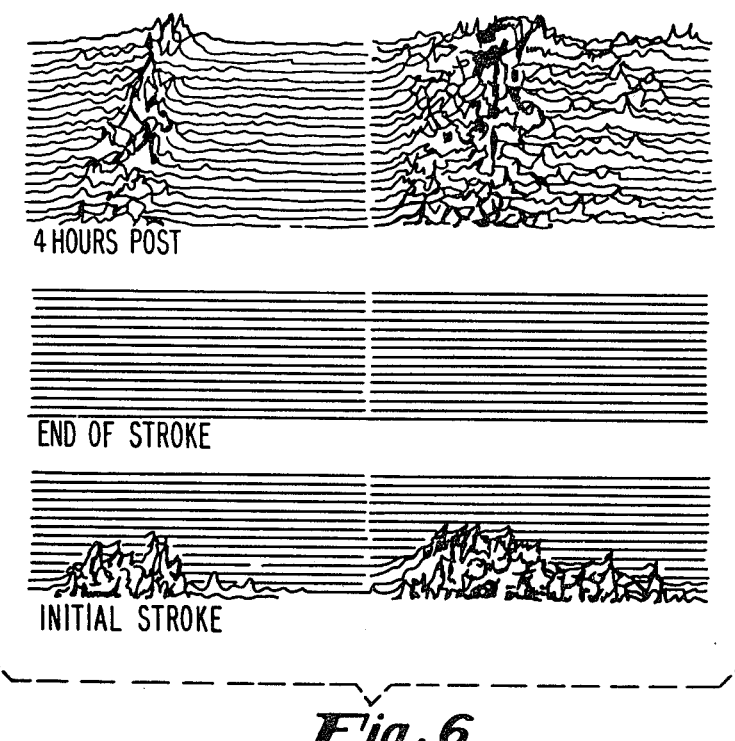
FIG. 6 is an EEG similar to FIG. 1 for an animal perfused with oxygenated nutrient emulsion having a $pO_2$ of 645 and showing an 88% return of electrocerebral power within 4 hours.

A fourth group of 7 cats was perfused with pump oxygenated nutrient solution (pO$_2$=645) at 6 ml/min. with withdrawal from the cisterna magna. All cats in this group regained some electrocerebral activity. The final total power which returned ranged from 5 to 88% of the prestroke base line (average 22%; p<0.01 compared to all non-oxygen groups). The electroencephalographic activity recovered generally throughout the 4 hour recovery period with the returning total cerebral power exhibiting a first order relationship as a function of time. At the observed recovery rate all animals should achieve completely normal EEG power spectra within 8 hours. An oxygen dependent EEG response is seen when non-oxygenated, bubble oxygenated (pO$_2$=400), and pump oxygenated (pO$_2$ =645) groups are compared as electrocerebral activity recovery greater than 5% was found in 10%, 62% and 100% respectively. FIG. 6 is an EEG tracing of the animal showing 88% return of electrocerebral activity within 4 hours after perfusion with oxygenated nutrient emulsion (pO$_2$=645). The asymmetry between hemispheres is an individual variation for this animal.

Figure 7:
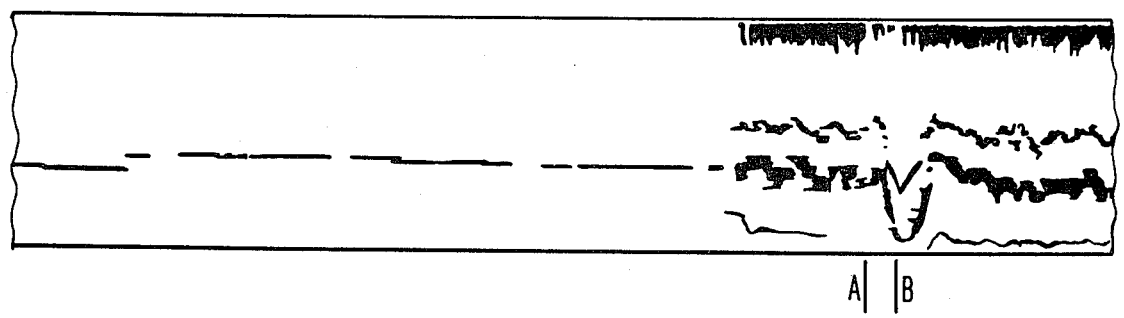
FIG. 7 is an EEG trace showing the effect on EEG activity of a temporary cessation in oxygenated nutrient emulsion circulation.

FIG. 7 is a portion of an EEG tracing showing the recorded effect on electro-cerbral activity of a temporary perfusion failure. This animal, which was perfused using the pump-oxygenated (pO$_2$=645) nutrient emulsion described above, experienced an interruption (pt. A) in perfusion for a time period of approximately 1 hour, whereupon perfusion was resumed (pt. B). As seen in this tracing a major deterioration of EEG activity occurred following cessation of perfusion, and resumed thereafter, confirming that the present method in fact sustains EEG activity.

Figure 8:
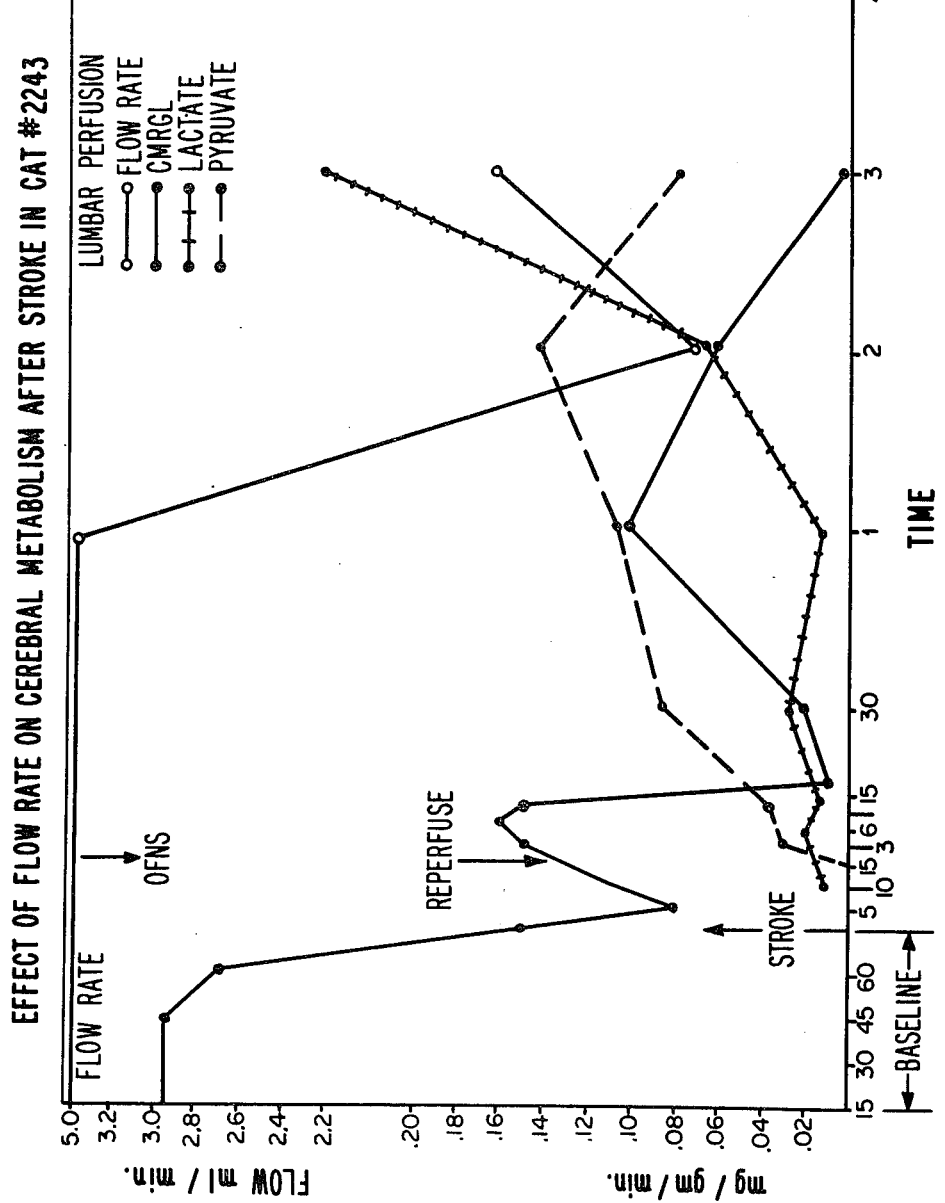
FIG. 8 is a graph showing the effect on glucose metabolism (CMRGl), lactate and pyruvate before and after stroke of a perfused animal particularly illustrating the effect of a reduction in perfusion rate to insubstantial levels.

In FIG. 8, the effect of a diminished perfusion flow rate of oxygenated nutrient emulsion is shown on the rate of glucose metabolism, and lactate and pyruvate concentration. In accordance with the above-described ventriculo-lumbar perfusion procedure using bubbled oxygenated (pO$_2$=400) nutrient emulsion, flow rate with nutrient emulsion without fluorocarbon was established at about 5.0 ml/min. A base line cerebral metabolic rate of glucose metabolism (CMRGI) was established prior to stroke, which was followed after 15 minutes with the perfusion of the oxygenated nutrient emulsion. CMRGl, which has recovered somewhat after 1 hour, is seen to decline rapidly as the flow rate of perfusate declines. Similarly, lactate levels rise precipitiously with flow rate decay. These results once again confirm that the flow of oxygenated nutrient emulsion through the cerebral spinal pathway should be maintained at acceptable rates in order to sustain neurologic tissue.

Figure 9:
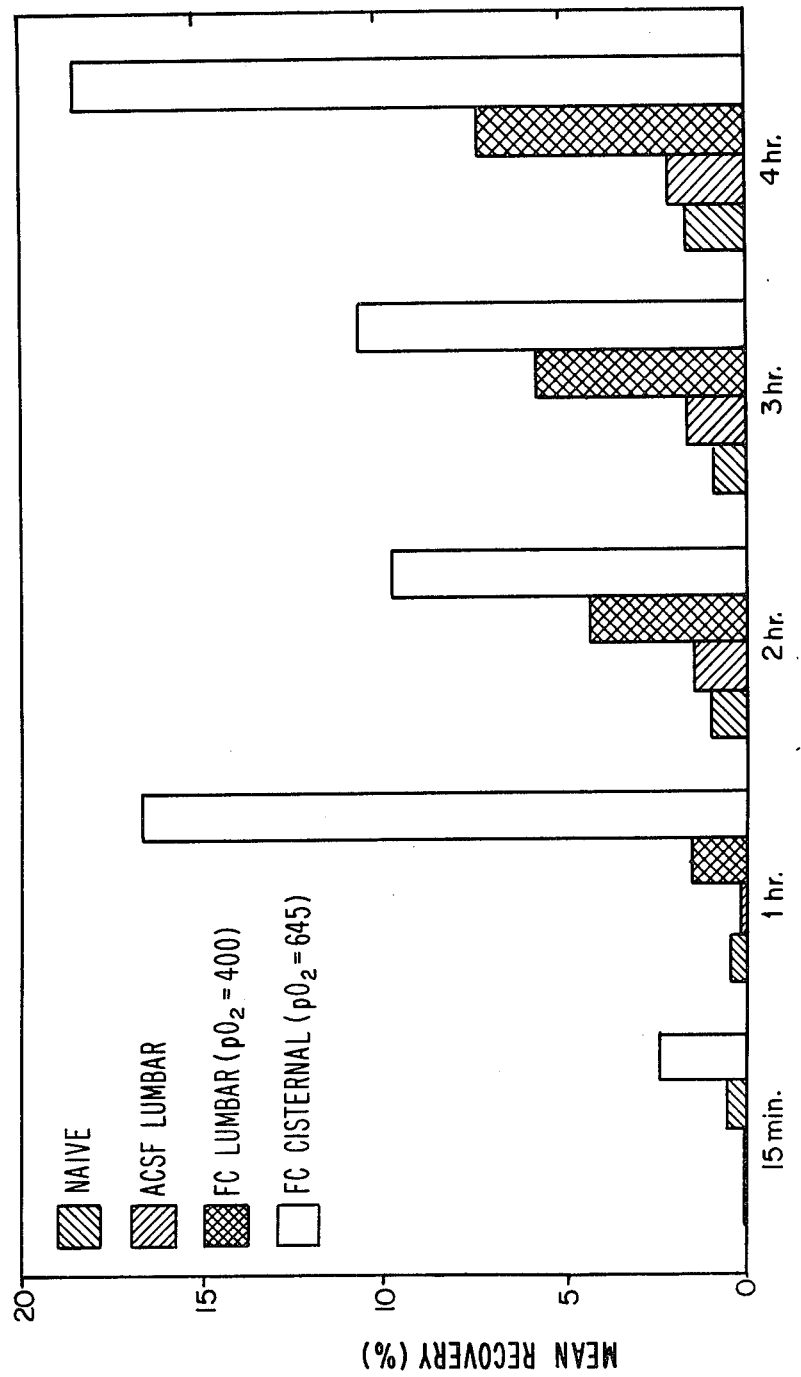
FIG. 9 is a bar graph showing the mean EEG recovery (percent) for groups of cats subjected to strokes resulting in 15 minutes of EEG isoelectricity, and comparing naive animals to those perfused only with artificial cerebral spinal fluid (lumbar) and oxygenated nutrient emulsion through lumbar and cisternal routes.

In FIG. 9, the mean recovery percent for the four groups of animals discussed above is presented in the form of a bar graph. It is presently preferred to insure that the pO$_2$ value of oxygenated nutrient emulsion upon input is great enough to insure that efficient oxygen transfer capabilities are maintained at the selected flow rate. For the FC lumbar group, exposure of oxygenated nutrient solution to certain tissue regions when its oxygen exchange value was below the known efficient oxygen exchange value (pO$_2$ less than 200) for the fluorocarbon component of this material may have occurred. This may be true even though the mean oxygen exchange value of the withdrawn emulsion is above 200. Accordingly, it is presently preferred to maintain the pO$_2$ value of withdrawn oxygenated nutrient emulsion at twice this minimum, or at above 400, either by raising the input $pO_2$ value to much higher levels, as with the ventriculo-cisternal animals described above, or by increasing the flow rate of oxygenated nutrient emulsion through the animal to maintain those values. In smaller animals, such as cats, the size of the cerebro spinal pathways creates hydraulic resistance which limits the flow rates which may be achieved at atmospheric pressures using certain pathways. In such animals, higher oxygen exchange values and shorter perfusion routes, such as the ventriculo-cisternal perfusion route, are preferred. In larger animals, such as humans, it is not anticipated that flow rates will be so limited. Nonetheless, high $pO_2$ values (at least 50% preferably 80+% of the maximum obtainable $pO_2$) are preferred to minimize the volume of perfusate necessary to perform a given treatment and to provide an additional margin of safety at the selected flow rate.

Samples of the perfusing fluids for the animals of this example were removed at predetermined times from entry and exit perfusion ports for analysis of lactate and pyruvate under a single blind condition. The results are summarzied in Table IV:

TABLE IV

Levels of lactate and pyruvate in cerebral spinal fluid perfusate before (baseline), during (isoelectric) and following (reflow) global ischemia in cats. Data are expressed in mg per 100 ml of perfusate and the values are means ± standard error. Six animals were perfused with NS[1] and 7 with OFNS[2] solution. After collecting the perfusate in tubes a 4#C, the samples were stored at −80° C. for analysis. Lactate and Pyruvate were assayed by the Sigma Method (Sigma Technical Bulletin #726, Oct. 1968 and #862, Oct. 1969) and conducted by Jefferson University Clinical Laboratories.

| Experimental Period | Lactate | | Pyruvate | | Lactate Pyruvate Ratio | |
|---|---|---|---|---|---|---|
| Baseline+ | 3.6 ± 1.1* | | 0.5 ± 0.1 | | 7.2 | |
| Isoelectric+ | 8.1 ± 1.9* | | 0.5 ± 0.1 | | 16.2 | |
| | NS | OFNS | NS | OFNS | NS | OFNS |
| Reflow (5 min) | 21.9 ± 11 | 10.0 ± 1.0 | 0.5 ± 0.1 | 1.2 ± 0.6 | 43.8 | 8.3+ |
| Reflow (4 hr) | 8.9 ± 3.3 | 10.4 ± 3.8 | 0.5 ± 0.1 | 1.7 ± 0.7 | 17.8 | 6.1 |

*During baseline and isoelectric time periods all cats were perfused with NS.
+p < 0.01 when compared to baseline lactate. p < 0.025 when compared to the ratio of reflow (5 min) perfused with NS.
[1]As used herein, NS refers to the nutrient solution of Example 1 without fluorocarbon component.
[2]As used herein, OFNS refers to the preferred oxygenated, fluorocarbon nutrient emulsion of Example 1.

In animals perfused with nutrient solution without fluorocarbon the concentration of lactate during the actual stroke (isoelectro) was of the normal CSF value. The lactate level rose percipitiously, an additional 440%, within 5 minutes of restoring the blood pressure and blood flow through the carotid arteries. Thereafter the level declined during the 4 hour period to 147% of base line. In contrast to the lactate data, the pyruvate concentration remained constant through the perfusion period.

When animals were perfused with oxygenated nutrient emulsion, on the other hand, the percipitious increase in lactate did not occur; instead there was a modest 52% rise during the initial 5 minute period, and the level thereafter remained stable. Significantly, in the oxygenated series the concentration of pyruvate more than doubled during the initial 5 minutes and continued to increase gradually during the remainder of the 4 hour period. The net production of lactate and pyruvate are often used as indictators of anarobic and aerobic glycolysis, respectively. Since these compounds change under different circumstances the expression of lactate/pyruvate (L/P) ratio best illustrates the net metabolic effects. A high L/P ratio indicates that anarobic glycolysis predominates. It is common practice, therefore, to use the L/P ratio as a sensitive indicator of the redox state of cells. Perfusion oxygenation in accordance with the present inventions significantly ($p \leq 0.01$) lowered the L/P ratio when compared to non-oxygenation (8.3 vs. 43.8). It is further evident that the oxygenated 4 hour L/P ratio is additionally lowered, whereas the non-oxygenated values are still 5 times greater than the control.

Although the oxygenated nutrient perfusate transit time through the brain is only a few seconds, significant oxygen extraction does occur. It was determined by the $pO_2$ difference between inflow and outflow fluids that oxygenated nutrient emulsion lost $pO_2 = 210$ (mean) during its intracerebral passage. Also unique to the oxygenated nutrient emulsion studies was a rising carbon dioxide presence in the exit fluid which did not occur in non-oxygenated experiments. The $pCO_2$ rose 5 fold in these fluids over the four hour period ($pCO_2 = 6.0$ vs. 3.0). It is considered that the appearance of carbon dioxide is important since it is a normal product of aerobic metabolism.

Figure 10:
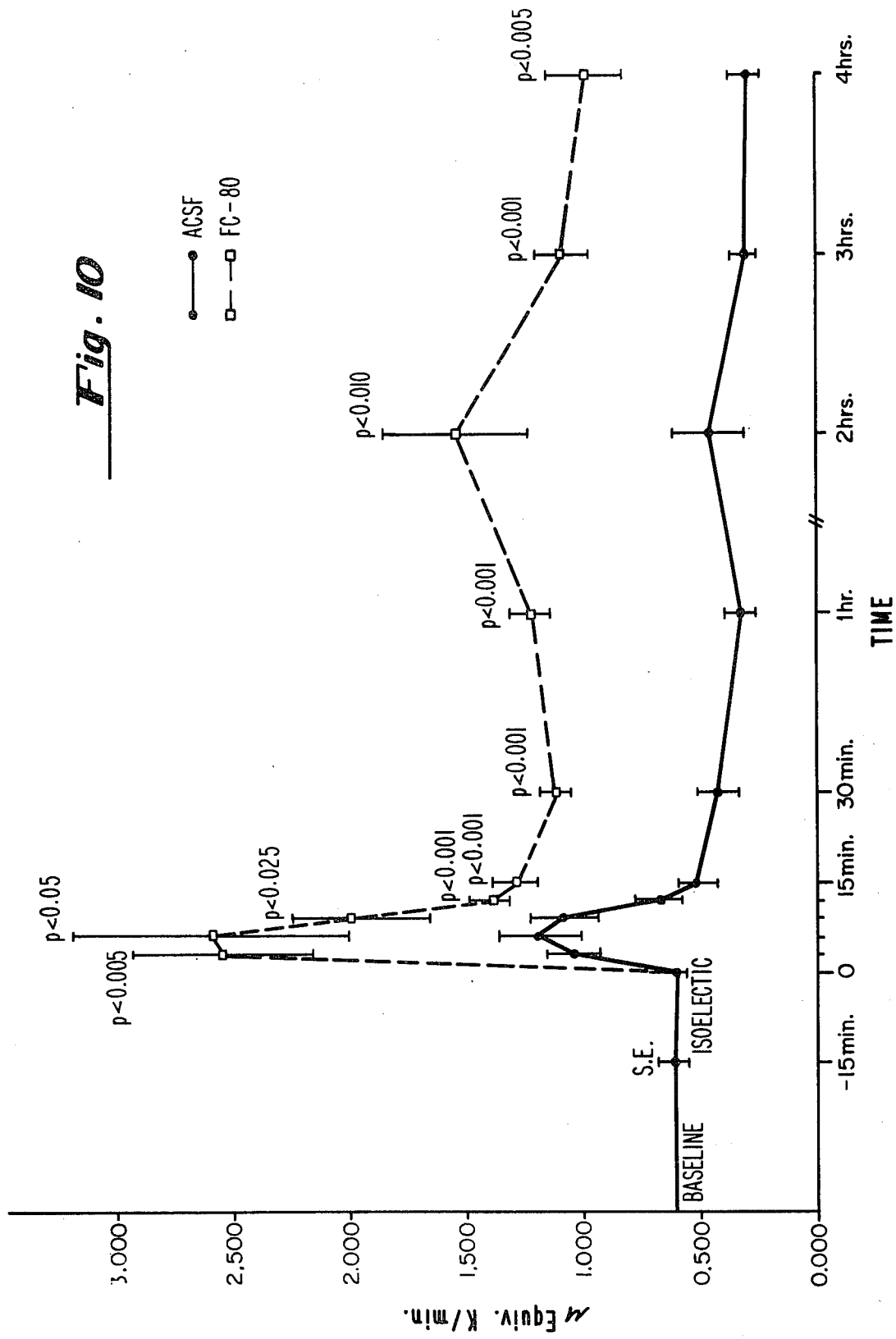
FIG. 10 is a graph of microequivalents of potassium per minute versus time for two experimental groups of cats subjected to 15 minutes of a stroke induced isoelectric state.
Figure 11:
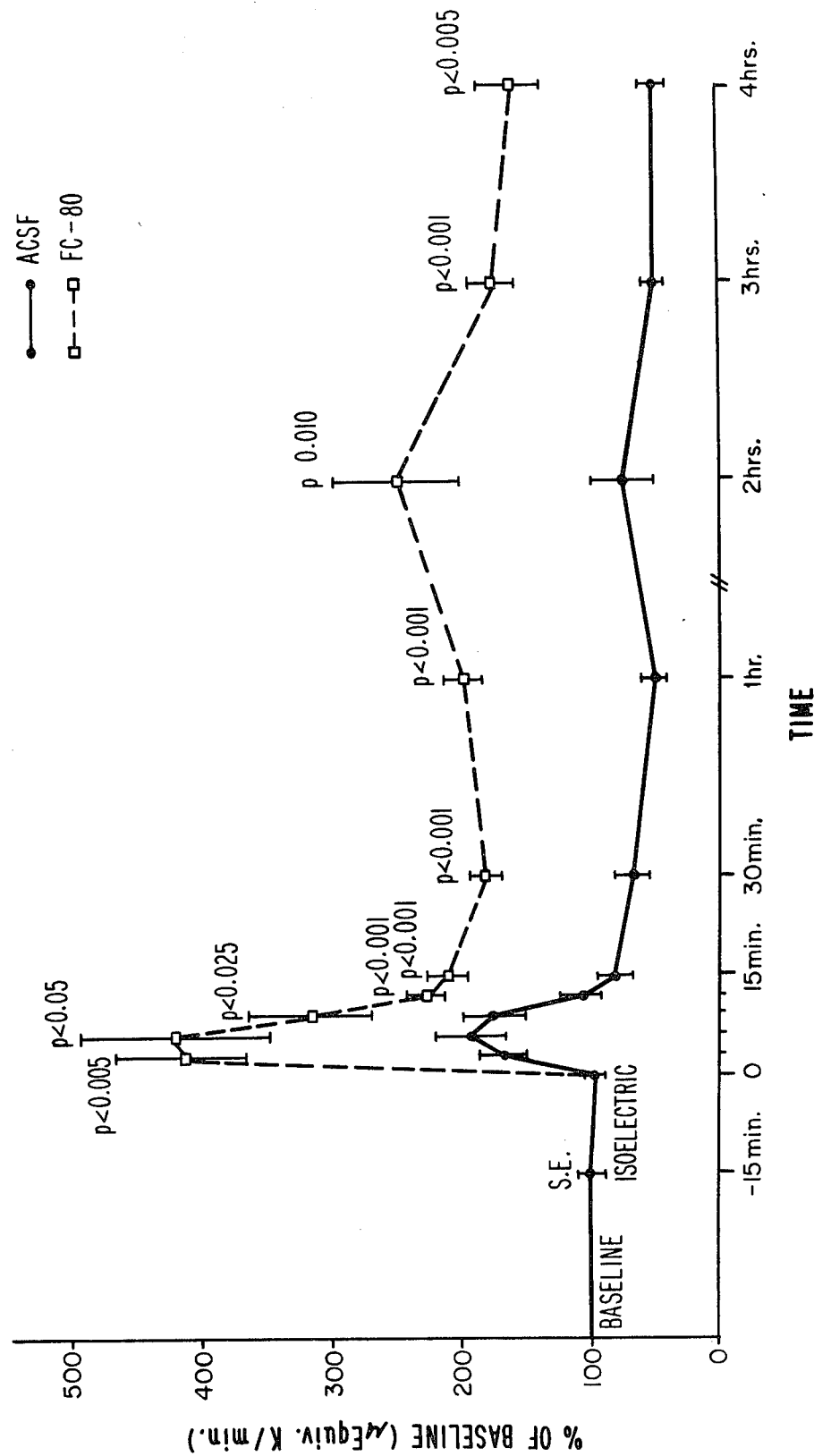
FIG. 11 is a graph similar to FIG. 10 wherein the data in FIG. 10 is represented as a percent of the base line figure.

In FIGS. 10 and 11 levels of potassium in perfusate before (base line), during (isoelectric) and following (reflow) global cerebral ischemia in cats are represented. Data are expressed in micro equivalents per minute, and the values are means ± standard error. Five animals were perfused with nutrient emulsion without fluorocarbon, and six with oxygenated fluorocarbon emulsion. After collecting the perfusate in tubes at 4° C., the samples were stored at −80° C. for analysis. Potassiums were assayed by atomic absorption spectrophotometry. During the base line and isoelectric time periods, all 11 cats were perfused with nutrient emulsion without fluorocarbon. There were no significant differences between isoelectric and base line levels of potassium in the perfusate. As seen from FIGS. 10 and 11, significant differences in the values of potassium were observed beginning almost immediately with perfusion (at time 0) and extending throughout the 4 hour experimental period.

Figure 12:
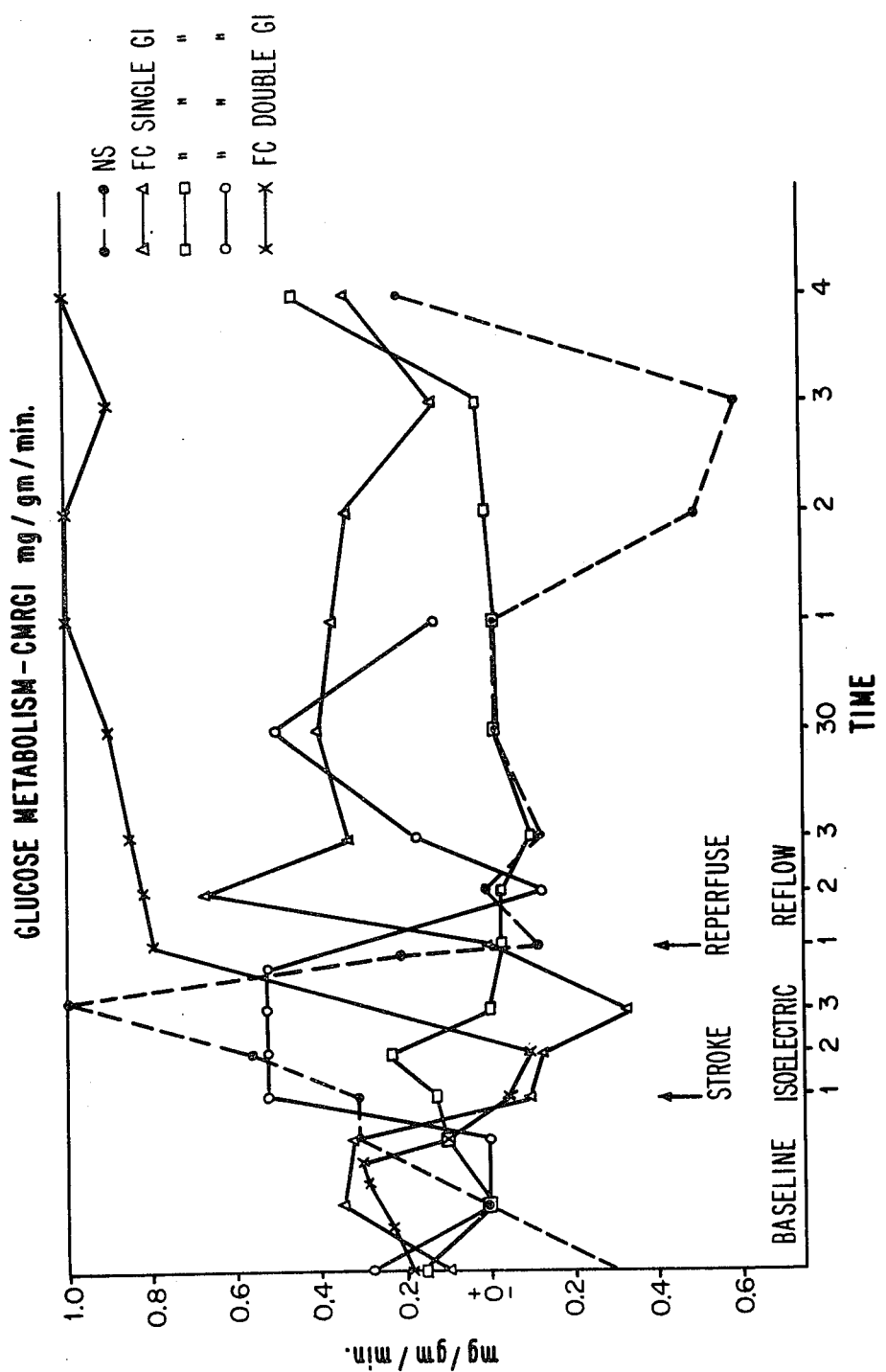
FIG. 12 is a glucose metabolism (CMRGl) graph plotting milligrams per grams per minute against time for three perfusions using a standard glucose concentration, one perfusion using twice that glucose concentration, and a control using artificial cerebral spinal fluid without fluorocarbon.

FIG. 12 discloses the effects on glucose metabolism for ventriculo-cisterna perfused animals subjected to the stroke and reperfusion procedure of this example. In accordance with the invention of Dr. John Lewis Alderman, one of these animals was perfused with twice the glucose concentration (372 mg %) of that used for the remaining animals described herein. As seen from FIG. 12, the glucose metabolism of animals provided with oxygenated nutrient emulsion (glucose = 186 mg %) is generally superior following reperfusion to the metabolism rate of the control receiving that solution without fluorocarbon. In view of the substantial increase in glucose metabolism exhibited by the animal having a "double glucose" solution (372 mg %), it is presently preferred to include at least such elevated glucose concentrations in perfusions performed in accordance with the method of the present invention.

These experimental results demonstrate that extravascular perfusion of oxygenated nutrient emulsion affects a significant reversal of the adverse cerebral metabolic effects induced by the experimental stroke condition. Coincident with the improve metabolic state electrocerebral activity returned. These findings indicate that extravascularly supplied oxygen, glucose and other nutrients were taken up and metabolized in amounts sufficient to restore high energy compounds and thereby reactivate membrane ionic pumps and reinstitute electrocerebral activity.

Oxygenated-fluorocarbon-nutrient-emulsion caused no detrimental effects on vital physiologic functions such as heart rate, blood pressure or electrocerebral (EEG) activity when perfused through the ventricular system for four hours of cats not subjected to the stroke paradigm. These animals exhibited no ill effects after 5-8 months, and were killed for a double blind neuropathologic examination of the brain, spinal cord and subarachnoid spaces. No gross or microscopic changes were observed and the specimens were indistinguishable from non-perfused animals.

In view of the above, those of ordinary skill in the art will recognize that various modifications can be made to the methods and apparatus described above without departing from the scope of the present invention. For example, it should be understood that, the injection and withdrawal catheters used to perform the herein described method should be sealed with respect to the skull so that a water and bacteria tight seal is created between these catheter and skull. Although conventional bone wax has been used for creating this seal in the feline experiments described above, fitting 22(a) preferably comprises a double threaded sleeve which is threaded into a bone aperture, and in turn receives complimental threads formed on injection catheter 20a. Such attachment means, particularly when used with a ventricular injection catheter, should eliminate any need for total head immobilization during human treatment.

It should also be understood that the oxygenated nutrient emulsions of the present invention may contain various therapeutic agents including free fatty acids, prostaglandins, prostacyclins, cyclic nucleotides and hormones.

As seen from the above, it is desired to maintain the the $pO_2$ level in the withdrawn fluid at levels which are substantially above the minimum level of efficient oxygen exchange of the subject fluorocarbon. For the fluorocarbon nutrient emulsion described above, that minimum (unsaturated condition) occurs at a $pO_2$ equal to about 190, which is about 30% of the readily achieved maximum $pO_2$ level. ($pO_2$ = 645) As described above, it is preferred to perform the treatment method of this invention so as to maintain the $pO_2$ of the withdrawn oxygenated nutrient emulsion at a $pO_2$ above 400, that is, at a $pO_2$ level which is about twice the minimum level of efficient oxygen exchange for the subject fluorocarbon. It is presently anticipated that a similar differential should be maintained in practicing the present invention utilizing oxygenated nutrient emulsions having other oxygenatable components exhibiting different ranges of efficient oxygen exchange.

The methodology described requires the formulation of a physiochemical fluid which must be adequately oxygenated, temperature controlled and delivered under well controlled conditions. The perfusion system of the present invention may be routinely placed by trained animal surgeons. Neurosurgeons commonly possess skills necessary to implant treatment ports in accordance with the present invention in humans. The procedure is relatively simple and can be quickly accomplished with available instruments. The oxygenated nutrient emulsion treatment delivery system of the present invention has certain similarities to the arterial heart-lung machine. Major differences, however, include the use of a complex synthetic fluid for cerebral spinal perfusion, the route performed by cerebral spinal perfusion is an extravascular one, and there is no known limitation on perfusion time in accordance with the herein disclosed method. Oxygenated fluorocarbon nutrient emulsion tolerates pumping mechanics well and the exit fluid can either be discarded or recirculated. Formed blood elements, on the other hand, are fragile and lyse under prolonged recirculation conditions. It is presently contemplated that cerebral-spinal fluid perfusion support will need to be carried out until the vascular system can once again take over. Surgical revascularization or bypass procedures will in some cases be necessary to accomplish this end. The return of cerebral vascular compentency can be assessed by measurements of regional blood flow, electro cerebral activity, and the metabolic configuration of the exit perfusion fluid. One foreseeable complication of this technique is bacterial infection, and rigorous attention to ambient sterility, millipore filtering, and antibiotics should reduce this hazard to acceptable levels. Safeguards have been built into the pumping system to immediately stop delivery if either the inlet or outlet become obstructed.

Conclusion

As seen from the above examples, and the foregoing description, circulation of the preferred embodiment nutrient liquid is capable of sustaining cellular integrity, aerobic metabolism and ongoing neuronal function. Even for neurons deep within the spinal cord (grey matter) the process has been successful in nurturing the ischemic neurons. The ability to sustain the central nervous system in a lethally ischemic field which persists for longer than a few minutes has never been accomplished before. The extravascular pathway has not been employed as a global nutrient route prior to the present invention, nor has the combined use of oxygen rich emulsion which also contains the other disclosed novel components been know to the art.

As seen from the above experiments, the methods, compositions and system of the present invention are capable of providing substantial amounts of oxygen to neurologic tissues to be treated, while at the same time, removing the by-products of aerobic metabolism, including carbon dioxide, which have been found to exist in substantially higher concentrations in the exit, diagnostic fluid. Similarly, as discussed above, rapid, normally lethal, lyses of anterior horn cells is readily preventable through the treatment of the present invention, protecting at least 60% of the cells through this modality. Similarly, high energy phosphate metabolism utilizing both oxygen and glucose is maintained at substantial levels. Accordingly, the methodology of the present invention represents a substantial advance in the treatment of central nervous system tissue. Prior to this invention there was not a method available to sustain central nervous tissues after a few minutes of profound ischemic insult. This invention should revolutionize the therapeutic capabilities by providing therapeutic approaches for stroke, aneurysm, brain injury, vasospasm, senility, tumors, coma, spinal cord injury, ischemia, post shock, post cardiac arrest and central nervous system poisoning.

It is further anticipated that the treatment method of the present invention should make it possible to interrupt the cerebral blood supply with some impunity for surgical maneuvers not heretofore possible without great attendant risk of producing cerebral infarction. Those of ordinary skill in the art will recognize that future development may result in perfection of the oxygenated nutrient emulsion composition, delivery rates, treatment times, the width of the therapeutic window in which treatment may be instituted and the correlation of behavioral functions in surviving animals with normalization of cerebral chemistry and electrographic activity. Nonetheless, by any standard, the present invention provides a dramatic, yet clinically acceptable, therapeutic method for treating ischemic neurologic tissue.

What is claimed is:

1. An artificial central nervous system, cerebrospinal pathway treatment liquid for treating hypoxic-ischemic cerebrospinal tissue, comprising, an aqueous emulsion containing:
   (a) a non-aqueous fluorocarbon oxygen transfer component for selectively combining with oxygen and for transferring oxygen to said tissues to be treated;
   (b) an aqueous nutrient component comprising at least essential electrolytes for said tissue; and
   (c) an emulsification component for permitting the emulsification of said nutrient means with said oxygen transfer means; and at least one treatment agent selected from the group consisting of steroids and amino acids.

2. The invention of claim 1 wherein said aqueous nutrient means further comprises sodium, potassium and chloride.

3. The invention of claim 2 wherein said aqueous phase further comprises magnesium and calcium.

4. The invention of claim 1 wherein said nutrient liquid has pH of between 6.8 and 7.5.

5. The invention of claim 1 wherein said nutrient component further comprises a carbohydrate component containing at least glucose.

6. The invention of claim 5 wherein said carbohydrate component further comprises glucose.

7. The invention of claim 1 wherein said treatment component further comprises an antiobiotic agent.

8. The method of claim 7 wherein said antibiotic agent is bacitracin.

9. The invention of claim 1 wherein said nutrient component further comprises carbon dioxide.

10. The invention of claim 1 wherein said nutrient liquid, after oxygen saturation, has a $pO_2$ in excess of 400.

11. The invention of claim 10 wherein said nutrient liquid, after oxygen saturation, has a $pO_2$ in excess of 600.

12. The invention of claim 1 wherein said nutrient liquid, after oxygen saturation, has an osmolarity of between about 298 and 317.

13. The invention of claim 1 wherein said treatment liquid further comprises an amino acid component having at least one essential amino acid.

14. The invention of claim 13 wherein said essential amino acid is selected from the group consisting of:
   D—Glutamic Acid
   L—Glutamine
   DL—Serine
   D—Threonine
   D—Lysine
   D—Valine
   D—Leucine
   DL—Isoleucine
   D—Phenylalanine
   DL—Tyrosine
   D—Methionine 15. The invention of claim 14 wherein each of said essential amino acids comprise said amino acid component.

16. The invention of claim 1 wherein said nutrient component further comprises a pyruvate.

17. The invention of claim 1 wherein said nutrient component further comprises a carbohydrate derivative which is a metabolic precursor of a pyruvate.

18. The invention of claim 1 wherein said nutrient component further comprises a bicarbonate ion.

19. The invention of claim 1 wherein said nutrient liquid has an osmolarity of between 318 and 325 and is thereby useful to treat cerebral edema.

20. The invention of claim 1 wherein said treatment liquid further comprises a steroid.

* * * * *

UNITED STATES PATENT AND TRADEMARK OFFICE
CERTIFICATE OF CORRECTION

PATENT NO. : 4,446,154

DATED : May 1, 1984

INVENTOR(S) : JEWELL L. OSTERHOLM

It is certified that error appears in the above-identified patent and that said Letters Patent is hereby corrected as shown below:

Column 25, line 63, please delete "umbar" and substitute therefor --lumbar--

Signed and Sealed this

Thirteenth Day of November 1984

[SEAL]

Attest:

GERALD J. MOSSINGHOFF

Attesting Officer

Commissioner of Patents and Trademarks